(12) United States Patent
Tsurushita et al.

(10) Patent No.: US 9,540,442 B2
(45) Date of Patent: Jan. 10, 2017

(54) ANTIBODIES OR FUSION PROTEINS MULTIMERIZED VIA CYSTEINE MUTATION AND A MU TAILPIECE

(71) Applicant: JN Biosciences LLC, Mountain View, CA (US)

(72) Inventors: Naoya Tsurushita, Palo Alto, CA (US); J. Yun Tso, Menlo Park, CA (US)

(73) Assignee: JN Biosciences LLC, Mountain View, CA (US)

( * ) Notice: Subject to any disclaimer, the term of this patent is extended or adjusted under 35 U.S.C. 154(b) by 253 days.

(21) Appl. No.: 13/956,121

(22) Filed: Jul. 31, 2013

(65) Prior Publication Data

US 2014/0037621 A1 Feb. 6, 2014

Related U.S. Application Data

(60) Provisional application No. 61/679,045, filed on Aug. 2, 2012, provisional application No. 61/767,724, filed on Feb. 21, 2013.

(51) Int. Cl.
*C07K 16/28* (2006.01)
*A61K 39/395* (2006.01)

(52) U.S. Cl.
CPC ..... *C07K 16/2878* (2013.01); *A61K 39/39558* (2013.01); *C07K 2317/24* (2013.01);
(Continued)

(58) Field of Classification Search
None
See application file for complete search history.

(56) References Cited

U.S. PATENT DOCUMENTS 6,475,749 B1 11/2002 Morrison et al.
8,952,134 B2 * 2/2015 Tso et al.
(Continued)

FOREIGN PATENT DOCUMENTS

WO      WO 99/15549 A2      4/1999
WO      WO 2011/073692 A1   6/2011
WO      WO 2014/022592 A1   2/2014

OTHER PUBLICATIONS

Mekhaiel et al., Polymeric human Fc-fusion proteins with modified effector functions, Sci. Reports, 1:124, Oct. 2011.*
(Continued)

*Primary Examiner* — Claire Kaufman
(74) *Attorney, Agent, or Firm* — Alston & Bird LLP

(57) ABSTRACT

The invention provides constant regions incorporating a cysteine mutation and linked to a μ tailpiece and antibodies or fusion proteins incorporating the same. The constant regions include at least CH2 and CH3 regions of an IgG heavy chain constant region including a cysteine mutation and μ tailpiece. Antibodies or fusion proteins incorporating the constant regions gains the ability to form multivalent complexes, e.g., pentameric or hexameric structures. Antibodies or fusion proteins incorporating the constant regions also retain IgG properties including specific binding to protein G, which facilitates purification and may exhibit pH-dependent FcRn binding, which is associated with a relatively long in vivo half-life. Depending on the isotype and subtype, the nature of the antigen and presence of an additional IgG hinge domain, such antibodies or fusion proteins may also have properties of specific binding to protein A, and effector functions such as ADCC, CDC and opsonization.

21 Claims, 11 Drawing Sheets

(52) U.S. Cl.
CPC ...... *C07K 2317/31* (2013.01); *C07K 2317/35* (2013.01); *C07K 2317/524* (2013.01); *C07K 2317/526* (2013.01); *C07K 2317/75* (2013.01); *C07K 2319/70* (2013.01)

(56) References Cited

U.S. PATENT DOCUMENTS

| | | | |
|---|---|---|---|
| 2002/0147326 | A1 | 10/2002 | Chaikin et al. |
| 2009/0068178 | A1* | 3/2009 | Crowley et al. |
| 2010/0297103 | A1* | 11/2010 | Murakami |
| 2012/0003210 | A1 | 1/2012 | Farrington et al. |
| 2013/0089547 | A1 | 4/2013 | Tso et al. |

OTHER PUBLICATIONS

Holler et al., Two adjacent trimeric Fas ligands are required for Fas signaling and formation of a death-inducing signaling complex, Mol. Cell. Biol. 23(4):1423-1440, 2003.*

InvivoGen, Immunoglobulin G Review [online], [retrieved Jun. 12, 2015], Retrieved from Internet<URL: http://www.invivogen.com/review-antibody-generation>, 2011.*

Smith et al., Addition of a mu-tailpiece to IgG results in polymeric antibodies with enhanced effector functions including complement-mediated cytolysis by IgG4, J. Immunol. 154:2226-2236, 1995.*

Ashkenazi, A, Directing cancer cells to self-destruct with pro-apoptotic receptor agonists, Nat. Rev. Drug Discov. 7:1001-1012, 2008.*

JN Biosciences, MultYmab™ technology:A novel antibody engineering platform to generate multimeric IgG antibodies with potent agonist activities, JN Biosciences, 2014.*

Kadekoppala et al., Merozoite surface proteins of the malaria parasite: The MSP1 complex and the MSP7 family, Int. J. Parasitol. 40:1155-1161, 2010.*

Kern et al., GA101 induces NK-cell activation and antibody-dependent cellular cytotoxicity more effectively than rituximab when complement is present, Leuk. Lymphoma, 54(11):2500-2505, Nov. 2013.*

GenBank: Accession No. AAL96415.1, "Immunoglobulin heavy chain variable region, partial [Papio anubis]," Mar. 27, 2002.

GenBank: Accession No. ACU1253.1, "Anit-beta-amyloid peptide immunoglobulin heavy chain variable region [Mus musculus]," Aug. 11, 2009.

WIPO Application No. PCT/US2013/053086, PCT International Preliminary Report on Patentability issued Feb. 3, 2015.

WIPO Application No. PCT/US2013/053086, PCT International Search Report & Written Opinion of the International Searching Authority mailed Nov. 13, 2013.

Sanchez-Arevalo Lobo et al., "Enhanced antiangiogenic therapy with antibody-collagen XVIII NC1 domain fusion proteins engineered to exploit matrix remodeling events," Int J . Cancer, 119:455-462, (2006).

EP Application No. 13825409.9 (Published as EP2880057), Supplementary European Search Report and European Search mailed Feb. 22, 2016.

* cited by examiner

Figs. 3A-F
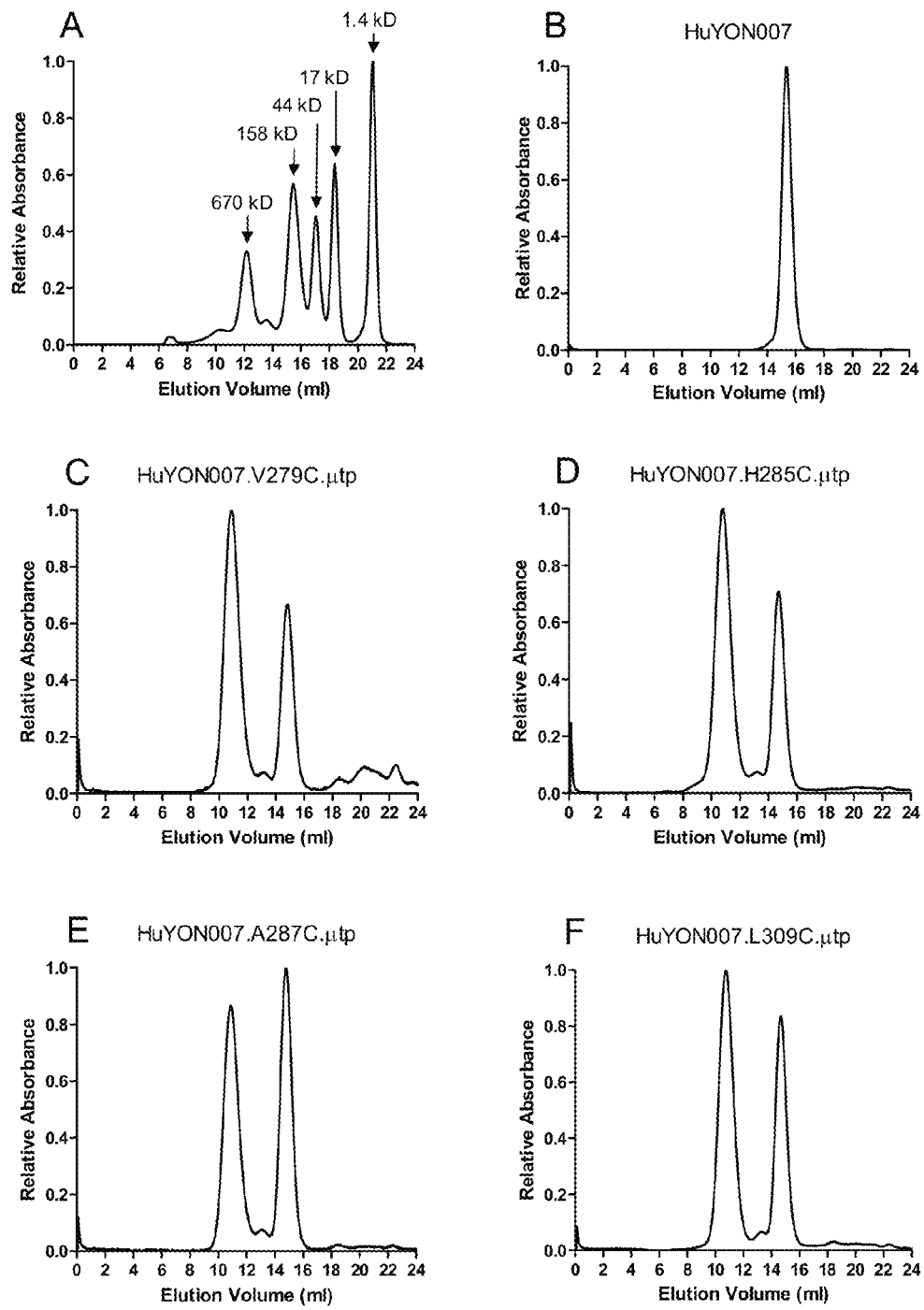

Figs. 4A-H
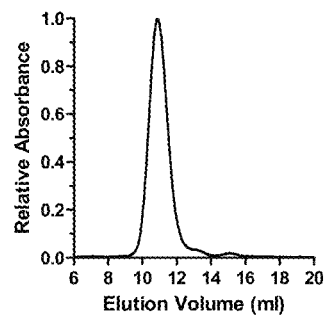
A  HuYON007.V279C.µtp Multimer
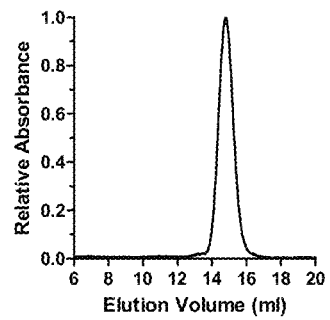
B  HuYON007.V279C.µtp Monomer
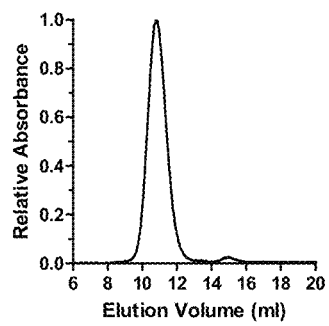
C  HuYON007.H285C.µtp Multimer
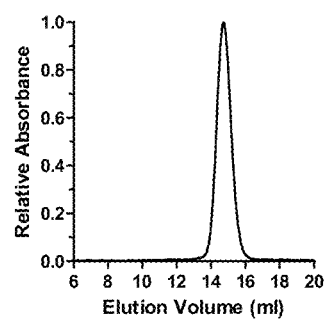
D  HuYON007.H285C.µtp Monomer
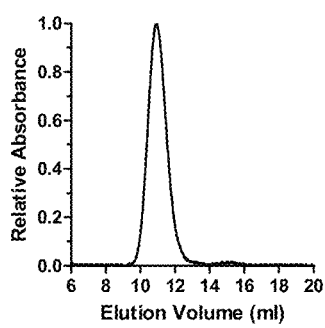
E  HuYON007.A287C.µtp Monomer
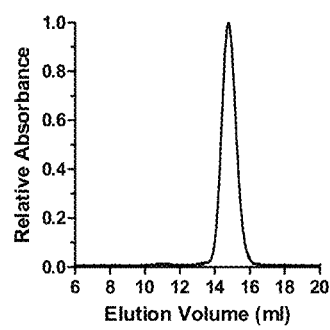
F  HuYON007.A287C.µtp Multimer
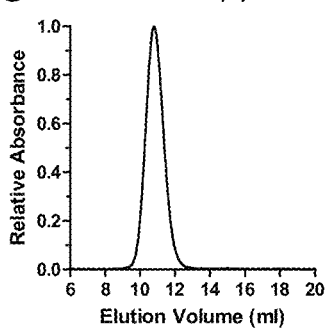
G  HuYON007.L309C.µtp Multimer
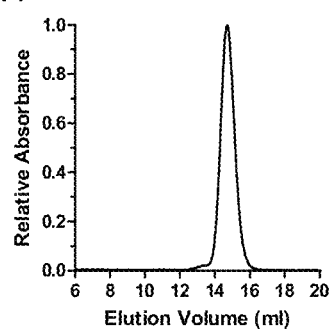
H  HuYON007.L309C.µtp Monomer Figs. 5A-D
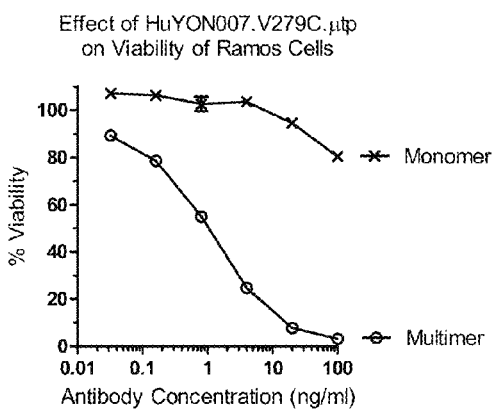
A.
Effect of HuYON007.V279C.µtp on Viability of Ramos Cells
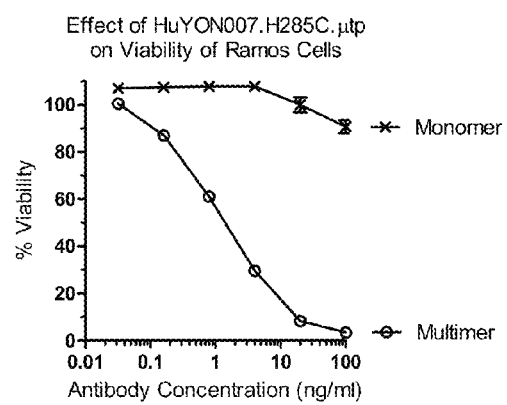
B.
Effect of HuYON007.H285C.µtp on Viability of Ramos Cells
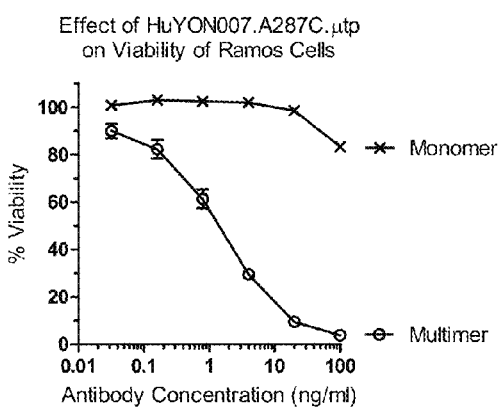
C.
Effect of HuYON007.A287C.µtp on Viability of Ramos Cells
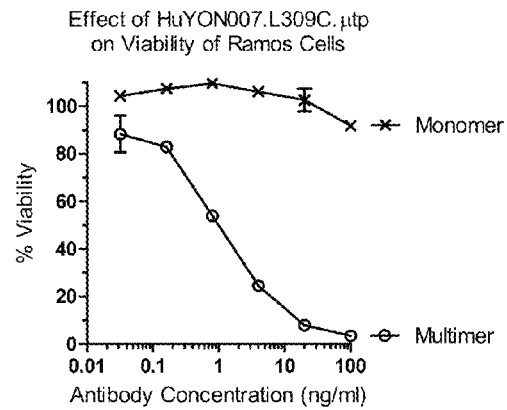
D.
Effect of HuYON007.L309C.µtp on Viability of Ramos Cells Figs. 6A-D
A.
Effect of HuYON007.V279C.µtp on Viability of Colo-205 Cells
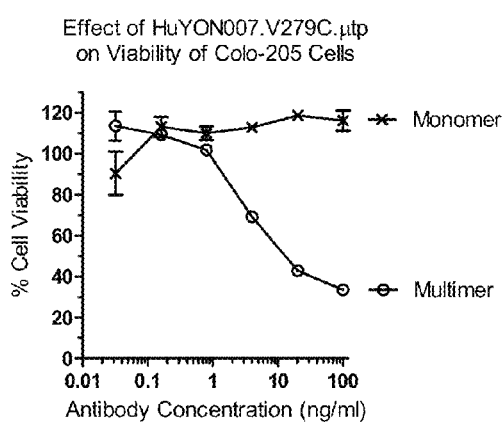
B.
Effect of HuYON007.H285C.µtp on Viability of Colo-205 Cells
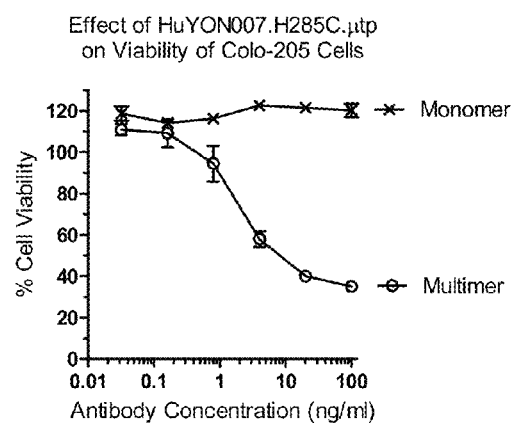
C.
Effect of HuYON007.A287C.µtp on Viability of Colo-205 Cells
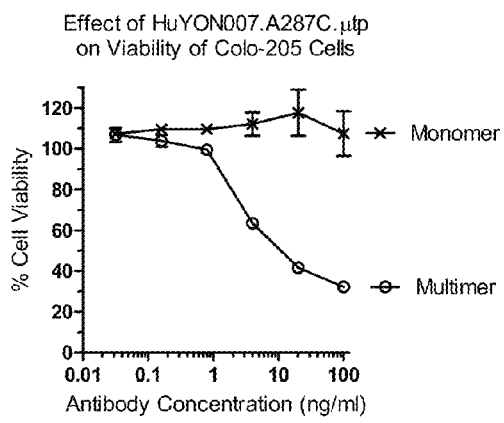
D.
Effect of HuYON007.L309C.µtp on Viability of Colo-205 Cells
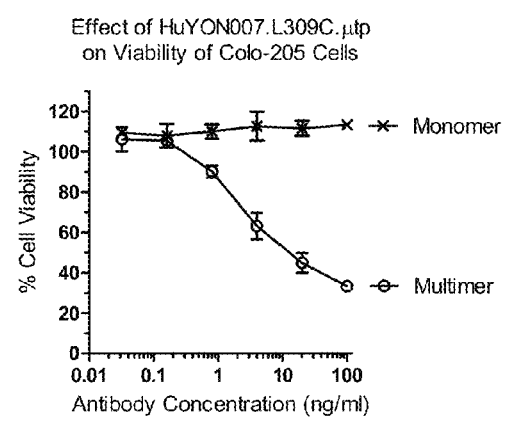

Figure 8A

Human gamma-1 heavy chain constant region

CH1:ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKV

Hinge:EPKSCDKTHTCPPCP

CH2:APELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK

CH3:GQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

Human gamma-2 heavy chain constant region

CH1:ASTKGPSVFPLAPCSRSTSESTAALGCLVKDYFPEPVTVSWNSGALTSGVHTFPAVLQSS
GLYSLSSVVTVPSSNFGTQTYTCNVDHKPSNTKVDKTV

Hinge:ERKCCVECPPCP

CH2:APPVAGPSVFLFPPKPKDTLMISRTPEVTCVVVDVSHEDPEVQFNWYVDGVEVHNAKTKP
REEQFNSTFRVVSVLTVVHQDWLNGKEYKCKVSNKGLPAPIEKTISKTK

CH3:GQPREPQVYTLPPSREEMTKNQVSLTCLVKGFYPSDIAVEWESNGQPENNYKTTPPMLDS
DGSFFLYSKLTVDKSRWQQGNVFSCSVMHEALHNHYTQKSLSLSPGK

Human gamma-3 heavy chain constant region

CH1:ASTKGPSVFPLAPCSRSTSGGTAALGCLVKDYFPEPVTVSWNSGALTSGVHTFPAVLQSS
GLYSLSSVVTVPSSSLGTQTYTCNVNHKPSNTKVDKRV

Hinge:ELKTPLGDTTHTCPRCPEPKSCDTPPPCPRCPEPKSCDTPPPCPRCPEPKSCDTPPPC
PRCP

CH2:APELLGGPSVFLFPPKPKDTLMISRTPEVTCVVVDVSHEDPEVQFKWYVDGVEVHNAKTK
PREEQYNSTFRVVSVLTVLHQDWLNGKEYKCKVSNKALPAPIEKTISKTK

CH3:GQPREPQVYTLPPSREEMTKNQVSLTCLVKGFYPSDIAVEWESSGQPENNYNTTPPMLDS
DGSFFLYSKLTVDKSRWQQGNIFSCSVMHEALHNRFTQKSLSLSPGK

Figure 8B

Human gamma-4 heavy chain constant region

CH1:ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRV

Hinge:ESKYGPPCPSCP

CH2:APEFLGGPSVFLFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKAK

CH3:GQPREPQVYTLPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK

Figure 8C

Human μ tailpiece
PTLYNVSLVMSDTAGTCY

J-Chain (aa1-22=signal peptide)
MKNHLLFWGVLAVFIKAVHVKAQEDERIVLVDNKCKCARITSRIIRSSEDPNEDIVERNI
RITVPLNNRENISDPTSPLRTRFVYHLSDLCKKCDPTEVELDNQIVTATQSNICDEDSAT
ETCYTYDRNKCYTAVVPLVYGGETKMVETALTPDACYPD

ANTIBODIES OR FUSION PROTEINS MULTIMERIZED VIA CYSTEINE MUTATION AND A MU TAILPIECE

CROSS-REFERENCE TO RELATED APPLICATIONS

The present application is a nonprovisional of 61/679,045, filed Aug. 2, 2012 and 61/767,724 filed Feb. 21, 2013, each of which is incorporated by reference in its entirety for all purposes.

INCORPORATION BY REFERENCE OF SEQUENCE LISTING

Sequences disclosed in this application are contained in a txt filed designated 436007_SEQLST.TXT of 107,944 bytes, created May 19, 2016, which is incorporated by reference.

BACKGROUND

Antibodies are glycoproteins produced by B cells that play an essential role in the immune system (Schroeder et al., J. Allergy Clin. Immunol. 125:S41-S52, 2010). Five classes of antibodies, namely IgM, IgD, IgG, IgA and IgE, are produced in mammals. In humans, four subclasses of IgG (IgG1, IgG2, IgG3 and IgG4) and two subclasses of IgA (IgA1 and IgA2) antibodies are produced. Each antibody is composed of two identical light chains and two identical heavy chains in the monomeric form. These four chains are connected to one another by a combination of covalent and non-covalent bonds, and form a Y-shaped molecule. There are two types of light chains, kappa and lambda, in mammals. Several different types of heavy chains exist that define the class of an antibody. In humans, the μ heavy chain is incorporated in IgM, the delta heavy chain in IgD, the gamma-1 heavy chain in IgG1, the gamma-2 heavy chain in IgG2, the gamma-3 heavy chain in IgG3, the gamma-4 heavy chain in IgG4, the alpha-1 heavy chain in IgA1, the alpha-2 heavy chain in IgA2, and the epsilon heavy chain in IgE. A monomeric form of these antibodies has two antigen binding sites, and thus is divalent for antigen binding. Although IgG, IgD and IgE are exclusively produced as a monomer, IgM is produced as a hexamer, and thus is dodecavalent for antigen binding, in the absence of J chains, and forms a decavalent pentamer when J chains are present (Gilmour et al., Trans. Med. 18:167-174, 2008). IgA forms a tetravalent dimer with a J chain, whereas IgA is a monomer when J chains are absent, although spontaneous formation of dimeric IgA without J chains has been reported (Johansen et al., Scand. J. Immunol. 52:240-248, 2000).

The U.S. Food and Drug Administration had approved thirty-one monoclonal antibodies as human therapeutics by the end of 2011. All of these therapeutic antibodies are IgG antibodies or derivatives thereof. Besides specific antigen binding, IgG antibodies elicit various biological functions mediated by the Fc region (Schroeder et al. supra; Desjarlais et al., Exp. Cell Res. 317:1278-1285, 2011). In humans, cell-bound IgG1 and IgG3 antibodies mediate antibody-dependent cell-mediated cytotoxicity (ADCC) by binding of the Fc region to Fcγ receptor type III (CD16) expressed on NK cells (Hulett et al., Adv. Immunol. 57:1-127, 1994). Likewise, cell-bound IgG1 and IgG3 antibodies can efficiently trigger complement-dependent cytotoxicity (CDC) by the interaction of the Fc region with complement components (Bindon et al., J. Exp. Med. 168:127-142, 1988).

The Fc region of all four subclasses of human IgG antibodies binds to the neonatal Fc receptor (FcRn), which is a heterodimer composed of a transmembrane a chain and β2-microglubulin, in a pH-dependent manner, resulting in rescuing IgG antibodies internalized by pinocytosis from catabolic degradation in lysosomes and allowing their recycling to the circulation (Ghetie et al., Annu Rev. Immunol. 18:739-766, 2000). IgG antibodies therefore exhibit slow clearance from the circulation which results in a long serum half-life, typically 23 days, in humans (Kindt et al., Chapter 4, Kuby Immunology, Sixth Edition, W. H. Freeman & Co., 2006). In addition, the Fc region of IgG antibodies bind to Protein A (except for IgG3) and Protein G, so that purification of IgG antibodies by Protein A or Protein G affinity chromatography is possible (Andrew et al., Unit 2.7, Chapter III, Current Protocols in Immunology, John Wiley & Sons, Inc. 1997).

Dimerization of specific molecules on the cell surface can often trigger one or more biological responses. Binding of monoclonal IgG antibodies to PSMA (prostate-specific membrane antigen) proteins on the cell surface increases the rate of PSMA internalization (Liu et al., Cancer Res. 58:4055-4060, 1998). Internalization and down-regulation of a type I transmembrane protein MUC1 is triggered by binding to a mouse IgG1 antibody (Hisatsune et al., Biochem. Biophys. Res. Commun. 388:677-382, 2009). Monoclonal antibodies against c-Met dimerize c-Met proteins on the cell surface and initiate intracellular signals resulting in cell proliferation (Prat et al., J. Cell Sci. 111:237-247, 1998). Likewise, a monoclonal anti-EPO receptor antibody can function as an agonist for cell growth by homodimerization of EPO receptors on the surface (Schneider et al., Blood 89:473-482, 1997). Antibody-mediated dimerization of Death Receptor 5 (DR5), a member of tumor necrosis factor receptor (TNFR) super-family, on the cell surface, however, does not always trigger signal transduction, while multimerization of DR5 proteins by a mixture of mouse monoclonal anti-DR5 IgG antibody and goat anti-mouse IgG polyclonal antibody, for example, induces signal transduction in the cytoplasm and triggers apoptosis (Griffith et al., J. Immunol. 162:2597-2605, 1999).

IgM antibodies exist as pentamers with J chains and hexamers without J chains (Gilmour et al., supra). In contrast to IgG antibodies, which are only capable of dimerizing antigens, IgM can multimerize cell surface proteins due to its decavalent or dodecavalent antigen binding capability. Monoclonal IgM antibodies with specificity for Fas, a member of the TNFR superfamily (Cosman, Stem Cells 12:440-455, 1994), can efficiently induce apoptosis of Fas-expressing cells due to multimerization of Fas proteins on the surface (Yonehara et al., J. Exp. Med. 169:1747-1756, 1989) while anti-Fas IgG antibodies do not unless they are cross-linked (Matsuno et al., J. Rheumatol. 29:1609-1614, 2002). Compared to IgG, IgM exhibits a much shorter circulation half-life, typically 5 days in humans, because of its inability to bind to FcRn (Kindt et al., supra). IgM antibodies are also unable to mediate ADCC due to the lack of binding to CD16. In addition, the lack of binding to Protein A and Protein G by IgM makes it impossible to purify IgM by Protein A and Protein G affinity chromatography, respectively (Gautam et al., Biotechnol. Adv. 29:84-849, 2011).

A variety of structural formats have been utilized in an attempt to generate novel forms of multivalent antibodies. Recent advances in the engineering of multivalent antibodies are summarized in a review paper of Cuesta et al. (Trends Biotech., 28:355-362, 2010). Preferred multivalent IgG antibodies are able to multimerize antigens efficiently on the cell surface. It is also important that the properties mediated by the Fc region of gamma heavy chains, such as ADCC, CDC, opsonization, pH-dependent FcRn binding, and the ability to bind to Protein A and Protein G, are maintained in such multivalent IgG antibodies.

To generate a multivalent IgG antibody, Caron et al. (J. Exp. Med., 176:1191-1195, 1992) introduced a serine-to-cysteine substitution at the fourth position from the carboxyl terminal of human gamma-1 heavy chain in the humanized anti-CD33 IgG1/kappa antibody, HuG1-M195. Such modified HuG1-M195, termed Hd-IgG, was purified and subjected to Ellman's Reagent (Pierce Chemical Co., Rockford, Ill.) for crosslinking and then blocking of excess sulfhydryl sites. Monomeric HuG1-M195 was eliminated from Hd-IgG by phenyl Sepharose column chromatography. The resultant Hd-IgG showed a dramatic improvement in the ability to internalize CD33 molecules and was more potent than HuG1-M195 at ADCC and CDC.

Miller et al. (J. Immunol., 170:4854-4861, 2003) constructed a tetravalent IgG antibody by duplicating the VH—CH1 region in the heavy chain of the humanized anti-HER2 IgG1 monoclonal antibody, hu4D5. The modified gamma heavy chain was composed of, from the N-terminus to the C-terminus, the VH, CH1, VH, CH1, hinge, CH2 and CH3 regions. One light chain bound to each of the four VH—CH1 regions in the modified IgG, forming a tetravalent hu4D5 antibody (TA-HER2). TA-HER2 was internalized more rapidly than the parental divalent hu4D5 on HER2-expressing cells. Miller et al. (supra) also constructed a tetravalent anti-DR5 IgG antibody, termed TA-DR5, in the same heavy chain format as in TA-HER2. TA-DR5 triggered apoptosis at ~100-fold lower concentration than the parental divalent anti-DR5 IgG monoclonal antibody.

Rossi et al. (Cancer Res., 68:8384-8392, 2008) reported the construction of a hexavalent anti-CD20 IgG antibody, designated Hex-hA20, using the Dock-and-Lock method. To generate Hex-hA20, which was composed of six Fab and two Fc regions, two components were constructed and separately produced in mammalian cells. First, the anchoring domain of the A-kinase anchoring proteins (AD) was genetically fused to the carboxyl terminus of the heavy chain in the humanized anti-CD20 IgG1 antibody, hA20. This construct was designated CH3-AD2-IgG-hA20. Second, the docking domain of the cyclic AMP-dependent protein kinase (DDD) was genetically fused to the carboxyl terminus of the Fab fragment of h20. This construct was designated CH1-DDD2-Fab-hA20. CH3-AD2-IgG-hA20 and CH1-DDD2-Fab-hA20 were purified by Protein A and Protein L affinity chromatography, respectively. Hex-hA20 was obtained by mixing purified CH3-AD2-IgG-hA20 and CH1-DDD2-Fab-hA20 under redox conditions followed by purification with Protein A. Hex-h20 inhibited proliferation of CD20-expressing B lymphoma cells lines without the need for a cross-linking antibody. Hex-h20 retained the ADCC activity of hA20, but lost the CDC activity.

Yoo et al. (J. Biol. Chem., 47:33771-33777, 1999) constructed variant human anti-DNS IgG2 antibodies in which part of the gamma-2 heavy chain was replaced with the corresponding part of the human alpha-1 heavy chain. In the construct termed γγγ-αtp, the 18-amino acid polypeptide present in the C-terminus of the human alpha-1 heavy chain, termed αtp (also called alpha tailpiece), was attached at the C-terminus of the human gamma-2 heavy chain. The γγγ-αtp construct was further modified to generate the following three variant IgG2 antibodies. In αγγ-αtp, the CH1 region of the gamma-2 heavy chain was replaced with the counterpart of the human alpha-1 heavy chain. In ααγ-αtp, the CH1, hinge and CH2 regions were replaced with the counterparts of the human alpha-1 heavy chain. In γαγ-αtp, the hinge and CH2 regions were replaced with the counterparts of the human alpha-1 heavy chain. These constructs were stably expressed in the mouse myeloma cell line Sp2/0 producing J chains. Each of purified γγγ-αtp, αγγ-αtp, ααγ-αtp and γαγ-αtp antibodies was a mixture of monomers, dimers, trimers, tetramers, pentamers and hexamers. The combined percentage of hexamers and pentamers in the mixture was 20% for γγγ-αtp, 25% for αγγ-αtp, 45% for ααγ-αtp, and 32% for γαγ-αtp.

Sorensen et al. (J. Immunol. 156:2858-2865, 1996) generated multivalent antibodies based on a human monoclonal anti-NIP (3-nitro-4-hydroxy-5-iodophenulacetic acid) IgG3 antibody variant in which the first, second and third hinge region are deleted. The gamma-3 heavy chain gene of this variant IgG3 antibody was modified in two locations. First, the 18-amino acid polypeptide present in the C-terminus of the human μ heavy chain, termed μtp (also called μ tailpiece), was attached at the C-terminus of the heavy chain. Second, a leucine residue at position 309 in the CH2 region was changed to a cysteine residue. Such modified monoclonal IgG3 antibody, called IgGL309Cμtp, was expressed in the mouse myeloma cell line J558L producing J chains, and purified using an NIP-Sepharose column. The secretion level was reported to be poorer for IgGL309Cμtp than for the parental IgG3 antibody, and a large fraction of IgGL309Cμtp was retained intracellularly. The size analysis showed that pentamers and hexamers constituted 81% of purified IgGL309Cμtp.

Sorensen et al. (Int. Immunol., 12:19-27, 2000) also modified the same human anti-NIP IgG3 antibody variant as described above by substituting the CH2 and CH3 regions of the gamma-3 heavy chain with the CH3 and CH4 regions, including μtp, of the human μ heavy chain. The heavy chain of such modified IgG3/IgM hybrid molecules, termed IgG-Cμ3-Cμ4, is composed of, from the N-terminus, the anti-NIP VH region, the CH1 and fourth hinge region of the human gamma-3 heavy chain, and the CH3 and CH4 regions, including μtp, of the human μ heavy chain. IgG-Cμ3-Cμ4 was expressed in J558L cells producing J chains and purified using an NIP-Sepharose column. Hexamers and pentamers constituted 14.0% and 66.7%, respectively, in purified IgG-Cμ3-Cμ4. Since IgG-Cμ3-Cμ4 does not have the CH2 and CH3 regions of the human gamma-3 heavy chain, it will lack Fcγ-mediated properties such as ADCC, pH-dependent FcRn binding, and the ability to bind to Protein A and Protein G.

There is a strong need of multimeric IgG antibodies, which are capable of inducing apoptosis, cytostasis and/or intracellular signal transduction by efficient cross-linking of cell surface proteins, such as TNF receptor family members (Hehlgans and Pfeffer, Immunol. 115:1-20, 2005; Mahmood and Shukla, Exp. Cell Res. 316:887-899, 2010), without losing Fcγ-mediated functions, such as ADCC, CDC, opsonization, and long serum half-life. Such multimeric IgG antibodies are expected to be effective for treatment of cancer and other diseases through their unique mechanisms of action.

SUMMARY OF THE CLAIMED INVENTION

The invention provides antibodies or fusion proteins comprising IgG CH2 and CH3 regions, wherein position 279, 285 or 287 of the Fc region by EU numbering is cysteine. Optionally, the CH3 region is linked to a human μ tailpiece at the C-terminus, wherein units of the antibody or a fusion protein can form a multimer by disulfide bonding between cysteines at the position in different units and between tailpieces in different units. Optionally, the IgG CH2 and CH3 regions are human IgG. Some antibodies or fusion proteins further comprise human IgG CH1 and hinge regions. Optionally, the human IgG CH1, hinge, CH2 and CH3 regions are human IgG1, human IgG2, human IgG3 or human IgG4. The antibody or fusion protein units can be held together by disulfide bonding between the cysteines at the position in different units and between the tailpieces in different units.

The invention further provides antibodies or fusion proteins comprising IgG hinge, CH2 and CH3 regions, wherein a position in the CH2 or CH3 region is mutated to a cysteine residue and the CH3 region is linked to a μ tailpiece at its C-terminus, wherein units of the antibody or fusion protein can multimerize via disulfide bonding between cysteines at the mutated position in different units and between tailpieces in different units. Some antibodies or fusion proteins further comprise an IgG CH1 region, preferably human IgG CH1. Optionally, the antibody or fusion protein specifically binds to a Death Receptor family protein and induces apoptosis of cells bearing the protein, such as DR4. Some antibodies or fusion proteins specifically binds to a TNF receptor family protein and induces apoptosis or cytostasis of cells bearing the protein.

The invention further provides antibodies or fusion proteins comprising human IgG1, 2 or 4 CH2 and CH3 regions, wherein a position in the CH2 or CH3 region is mutated to a cysteine residue and the CH3 region is linked to a μ tailpiece at its C-terminus, wherein units of the antibody or fusion protein can multimerize via disulfide bonding between cysteines at the mutated position in different units and between tailpieces in different units.

The invention further provides an antibody comprising a mature heavy chain variable region comprising the CDRs of SEQ ID NO:23 and a mature light chain variable region comprising the CDRs of SEQ ID NO:27. Optionally, the mature heavy chain variable region has at least 90% identity to SEQ ID NO:31 (without signal peptide) and the mature light chain variable region has at least 90% identity to SEQ ID NO:32 (without signal peptide).

The invention further provides an antibody comprising a mature heavy chain variable region having at least 90% identity to SEQ ID NO:31 (without signal peptide) and a mature light chain variable region having at least 90% identity to SEQ ID NO:32 (without signal peptide).

Any of the above antibodies or fusion proteins can be a single-chain antibody comprising a single-chain Fv linked to the heavy chain constant region. Optionally, the antibody is a component of a multi-specific antibody comprising a plurality of single-chain antibodies, wherein the scFvs of the plurality have different VH regions, and the plurality of single-chain antibodies are complexed in the multi-specific antibody via disulfide bonding between cysteines at the mutated position in different units and between tailpieces in different units. Optionally, the scFvs have the same VL region.

Any of the above antibodies or fusion proteins can specifically binds protein G, specifically binds protein A, exhibit ADCC, CDC and/or opsonization. Optionally, the CH1 region, if present, and the hinge region, and CH2 and CH3 regions are human IgG1 regions, and the antibody specifically binds protein G, and specifically binds protein A. Optionally, the antibody exhibits ADCC, CDC and opsonizaton.

In some of the above antibodies or fusion proteins, the CH1 region if present, and the hinge, CH2 and CH3 regions of human IgG2 or IgG4 isotype and the antibody or fusion protein specifically binds protein G and specifically binds protein A. Optionally, the antibody or fusion protein is a fusion protein comprising the immunoglobulin heavy chain linked to a heterologous polypeptide. Optionally, the heterologous protein is linked to the hinge of the constant region via a flexible linker, such as Gly-Gly-Ala-Ala (SEQ ID NO:66). Optionally, the heterologous polypeptide is a receptor extracellular domain or a protein that specifically binds to a receptor extracellular domain. Optionally, the fusion protein is a component of a multi-specific complex comprising a plurality of fusion protein, the fusion proteins including different heterologous polypeptides.

Any of the above antibodies or fusion proteins can be in the form of a multispecific complex comprising an antibody and a fusion protein complexed by disulfide bonding between the cysteines at the position and between μ tailpieces in different units.

Any of the above antibodies can be a humanized, chimeric, veneered or human antibody.

Any of the above antibodies or fusion proteins can specifically binds the extracellular domain of a receptor.

Some of the above antibodies or fusion proteins specifically bind to CD79a, CD30, DR5, DR4, CD40, OX40, 4-1BB, GIT or CD27.

Some fusion proteins comprise an extracellular domain of a TNF-alpha receptor, LFA-3 or an IL-1 receptor. Some fusion proteins comprise a TRAIL protein.

Any of the above antibodies or fusion proteins can be conjugated to a toxic moiety, optionally cytotoxic.

The invention further provides a pharmaceutical composition comprising an antibody or fusion protein as defined above.

The invention further provides a method of treating cancer comprising administering to a patient having or at risk of cancer an effective regime of an antibody or fusion protein as defined above.

The invention further provides a method of treating an immunological disorder comprising administering to a patient having or at risk of the disorder an effective regime of an antibody or fusion protein as defined above.

The invention further provides a method of producing a multi-specific complex of antibodies and/or fusion proteins, comprising a. transfecting a cell with a vector or vectors encoding a plurality of antibodies and/or fusion proteins as defined above, the antibodies and/or fusion proteins having different specificities; wherein the antibodies and/or fusion proteins are expressed and assembled into a multispecific complex via disulfide bonding between the cysteines at the position and between μ tailpieces; and b. isolating the multi-specific complex from the cell culture. Optionally, the plurality of antibodies or fusion proteins is encoded by a different vector.

The invention further provides a monoclonal antibody comprising a mature light chain variable region comprising CDRs having amino acid sequences designated SEQ ID NO. 39, 40 and 41 respectively and comprising a mature heavy chain variable region comprising CDRs having amino acid sequences designated SEQ ID NO. 43, 44 and 45 respectively.

The invention further provides a monoclonal antibody comprising a mature light chain variable region having at least 90% sequence identity to the mature variable region of SEQ ID NO. 38 and a mature heavy chain variable region having at least 90% sequence identity to the mature variable region of SEQ ID NO. 42.

BRIEF DESCRIPTION OF THE DRAWINGS

FIGS. 3A-F: Elution pattern of anti-DR5 IgG1 antibodies from a Superose 6 gel filtration column.

FIGS. 4A-H: Elution pattern of monomeric and multimeric anti-DR5 IgG1 antibodies from a Superose 6 gel filtration column.

FIGS. 5A-D: Induction of apoptosis of Ramos cells by multivalent anti-DR5 IgG1 antibodies.

FIGS. 6A-D: Induction of apoptosis of Colo-205 cells by multivalent anti-DR5 IgG1 antibodies.

FIGS. 8 A, B, C: Sequences of IgG and IgM components. FIG. 8A shows the human gamma-1 heavy chain constant region CH1, hinge, CH2, and CH3 domains (SEQ ID NOS:48-51, respectively), the human gamma-2 heavy chain constant region CH1, hinge, CH2, and CH3 domains (SEQ ID NOS:52-55, respectively), and the human gamma-3 heavy chain constant region CH1, hinge, CH2, and CH3 domains (SEQ ID NOs:56-59, respectively). FIG. 8B shows the human gamma-4 heavy chain constant region CH1, hinge, CH2, and CH3 domains (SEQ ID NOs:60-63, respectively). FIG. 8C shows the human μ tailpiece (SEQ ID NO:64) and the J-chain (SEQ ID NO:65).

DEFINITIONS

Figure 1:
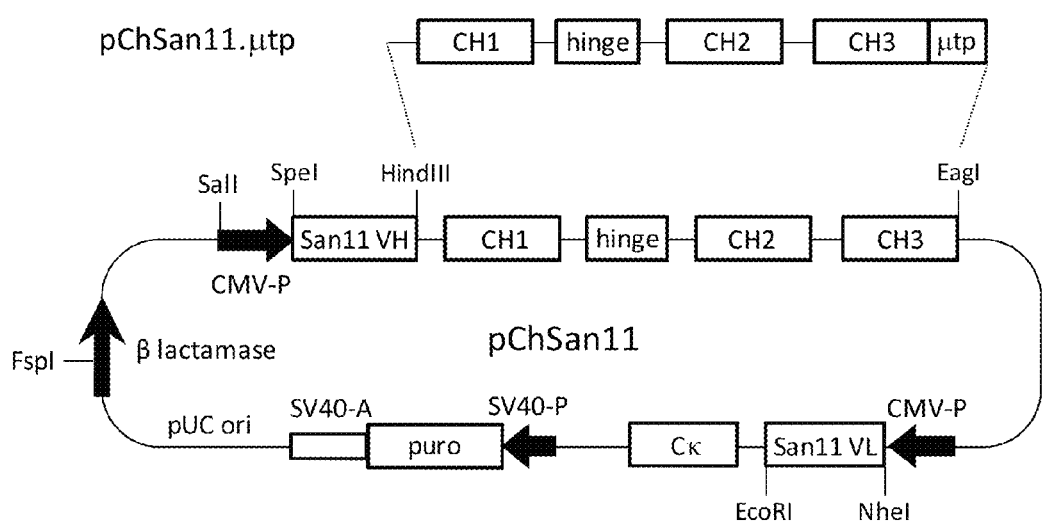
FIG. 1: Schematic structure of expression vectors for San11 antibodies.

Antibodies or fusion proteins are typically provided in isolated form. This means that an antibody or fusion protein is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Sometimes antibodies or fusion proteins are at least 60, 70, 80, 90, 95 or 99% w/w pure of interfering proteins and contaminants from production or purification. Often an antibody or fusion protein is the predominant macromolecular species remaining after its purification.

Specific binding of an antibody or fusion protein to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody or fusion protein binds one and only one target.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the antibodies or fusion proteins of the invention have been expressed and secreted. A pair of heavy and light chain variable regions defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. In IgA, the heavy constant region is divided into CH1, CH2 and CH3. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcRn binding. In IgM antibodies, the μ heavy chain constant region (Cμ) is subdivided into four regions Cμ1, Cμ2, Cμ3 and Cμ4. The Cμ3 and Cμ4 regions, sometimes in combination with one or more J chains, provide a multimerization function in natural IgM antibodies. The μ tailpiece is an 18 amino-acid-long polypeptide located at the C-terminus of a IgM heavy chain constant region. IgM multimerizes to form a pentameric structure in the presence of J chains and a hexameric structure in their absence.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" segment of about 12 or more amino acids, with the heavy chain also including a "D" segment of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is divalent. In natural antibodies, the binding sites are the same. However, bispecific antibodies can be made in which the two binding sites are different (see, e.g., Songsivilai and Lachmann, Clin. Exp. Immunol., 79:315-321 (1990); Kostelny et al., J. Immunol., 148:1547-53 (1992)). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chain variable regions or between different light chain variable regions are assigned the same number. Although Kabat numbering can be used for antibody constant regions, the EU index is more commonly used, as is the case in this application.

An antibody or fusion protein unit, also known as a multimerization unit, is the monomeric unit of an antibody or fusion protein incorporating a cysteine mutation and μ tailpiece subject to multimerization by disulfide bond formation between cysteine mutations in different units and tailpieces of different units. A multimerization unit can itself be mono or divalent. In a mono-specific divalent antibody unit, the two heavy chains and two light chains are the same. In a bispecific divalent antibody unit, there are two different heavy and light chain pairings with different binding specificities. An antibody unit can also be monovalent containing a single heavy and light chain combination, as is the case with single-chain antibodies in which the heavy and light variable regions pair intramolecularly. A fusion protein unit can be monomeric, homodimeric containing two copies of a fusion protein or heterodimeric, containing two different fusion proteins.

Multimerization means the association of at least two multimerization units and more typically five or six such units via disulfide bonding between mutant cysteines (i.e., one mutant cysteine in one unit bonds with a mutant cysteine in another) and between μ tailpieces (i.e., one μ tailpiece linked to one IgG in one unit disulfide bonds with a μ tailpiece in another unit). Multimerization of antibodies or fusion proteins with an IgG heavy chain constant region incorporating a cysteine mutation and linked at the C-terminus to a μ tailpiece (cys-μ heavy chain constant region) may sometimes form higher or lower order structures than the pentameric or hexameric structure of normal IgM. Such is sometimes indicated by characterizing a complex formed by multimerization as having at least about five or six units.

Valency refers to the number of binding regions or in other words, maximum number of molecules of a target antigen that can be bound by an antibody or fusion protein. A normal homodimeric IgG antibody has a valency of two. A normal IgM antibody has a valency of 10 or 12 depending on whether a pentameric or hexameric structure is formed (i.e., five or six IgM units, each being a tetramer with two binding sites). Antibodies or fusion proteins of the present invention in which the monomeric unit is bivalent, can have valencies of 10 or 12, whereas antibodies or fusion proteins in which the monomeric unit is monovalent can have valencies of 5 or 6. The valencies may vary from these values in that antibody or fusion proteins with cys-μ heavy chain constant regions may sometimes form higher or lower order structures than the pentameric or hexameric structure of normal IgM. These valencies are theoretical maxima. In practice, the numbers of copies of an antigen bound may be less than the theoretical maximum due to steric constraints.

An antibody or fusion protein of the invention is mono-specific if all of its antigen (or ligand) binding regions have the same specificity. An antibody or fusion protein is multispecific if its antigen binding regions include at least two different specificities. The number of different specificities in a multispecific antibody or fusion protein can range from 2 up to the maximum valency of the antibody or fusion protein (e.g., 10 or 12). In a population of antibodies or fusion proteins produced by the same cell culture, the number of different specificities can vary among different members of the population.

The term "antibody" includes any form of antibody with at least one binding region including monovalent fragments, divalent tetrameric units of two heavy chains and light chains, and higher order complexes, particularly pentamers and hexamers of monovalent or divalent units. An antibody can be mono-specific in which case all binding regions have the same specificity or multi-specific in which the binding sites have at least two specificities. Antibody fragments typically include a heavy chain variable region and cys-μ heavy chain constant region and may also include a light chain variable region. For example, an antibody fragment can include from N-terminal to C-terminal a light chain variable region, a peptide spacer, a heavy chain variable region and a cys-μ heavy chain constant region of the invention. Another fragment includes a heavy chain variable region (the binding region) and a cys-μ heavy chain constant region and no light chain (i.e., a Dab or nanobody). Likewise, a fusion protein includes a monomeric or dimeric fusion protein unit, or higher order complexes, particularly pentamers and hexamers.

The term "epitope" refers to a site on an antigen to which an antibody or fusion protein binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. Some antibodies bind to an end-specific epitope, meaning an antibody binds preferentially to a polypeptide with a free end relative to the same polypeptide fused to another polypeptide resulting in loss of the free end. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

The term "antigen" or "target antigen" indicates a target molecule bound by an antibody or fusion protein. An antigen may be a protein of any length (natural, synthetic or recombinantly expressed), a nucleic acid or carbohydrate among other molecules. Antigens include receptors, ligands, counter receptors, and coat proteins.

A heterologous polypeptide in a fusion protein is a polypeptide not naturally linked to an immunoglobulin constant region. Such a polypeptide can be a full-length protein or any fragment thereof of sufficient length to retain specific binding to the antigen bound by the full-length protein. For example, a heterologous polypeptide can be a receptor extracellular domain or ligand thereto.

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues.

Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): tip, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

The term "antibody-dependent cellular cytotoxicity," or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcγreceptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

The term opsonization also known as "antibody-dependent cellular phagocytosis," or ADCP, refers to the process by which antibody-coated cells are internalized, either in whole or in part, by phagocytic immune cells (e.g., macrophages, neutrophils and dendritic cells) that bind to an immunoglobulin Fc region.

The term "complement-dependent cytotoxicity" or CDC refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

pH-dependent binding of an antibody to an FcRn receptor means that an antibody binds more strongly to such a receptor at pH 6.0 than at pH 7.5. Binding of FcRn at a low pH in endosomes after internalization by pinocytosis rescues IgG antibodies from catabolic degradation in lysosomes. Rescued IgG antibodies are then released from FcRn at a neutral pH and recycled to the circulation. Such pH-dependent FcRn binding is the basis of the molecular mechanism for a long serum half-life of IgG antibodies (and antibodies and fusion proteins incorporating cys-g heavy chain constant regions of the invention) (Ghetie et al., Annu Rev. Immunol. 18:739-766, 2000). For example, human IgG antibodies bind to human neonatal Fc receptors (FcRn) at pH 6.0 while they bind only weakly to FcRn at pH 7.5. The FcRn binding site in IgG antibodies lies at the junction of the CH2 and CH3 domains. Because a μ heavy chain does not bind to FcRn at pH 6.0 or 7.5, natural IgM cannot take advantage of the FcRn-mediated pathway to rescue antibodies from degradation in lysosomes and therefore in general have shorter half-lives than natural IgG antibodies.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

A human antibody can be isolated from a human, or otherwise result from expression of human immunoglobulin genes (e.g., in a transgenic mouse, in vitro or by phage display). Methods for producing human antibodies include the trioma method of Oestberg et al., Cys muoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, Nature 148, 1547-1553 (1994), Nature Biotechnology 14, 826 (1996), Kucherlapati, WO 91/10741 (1991) and phage display methods (see, e.g. Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332.

Protein A is a 40-60 kDa surface protein originally found in the cell wall of the bacterium Staphylococcus aureus. Protein A specifically binds with high affinity to human IgG1, IgG2 and IgG4 as well as mouse IgG2a and IgG2b. It does not bind to human IgG3 or IgA, or IgM. Protein A is used for affinity purification of antibodies.

Protein G is a 65-kDa (G148 protein G) and a 58 kDa (C40 protein G) Streptococcal cell surface protein. It contains a serum albumin binding domain not needed for IgG binding, which is often deleted. Protein G specifically binds to all of the human IgG isotypes but not IgA or IgM. Protein G is also useful for antibody purification.

When an antibody of the invention (present antibody) is said to retain a property of a parental antibody from which it was derived (i.e., without mutant cysteine and μ tailpiece), retention can be partial or complete. Complete retention of an activity between a present antibody of the invention and a parent antibody from which it was derived means the activity of the present antibody is the same within experimental error or greater than that of the parent antibody. Partial retention of activity means that an activity of the present antibody is significantly above background level of a negative control (i.e., beyond experimental error) and preferably at least 50% of the corresponding activity of the parent antibody.

DETAILED DESCRIPTION

I. General

Figure 7:
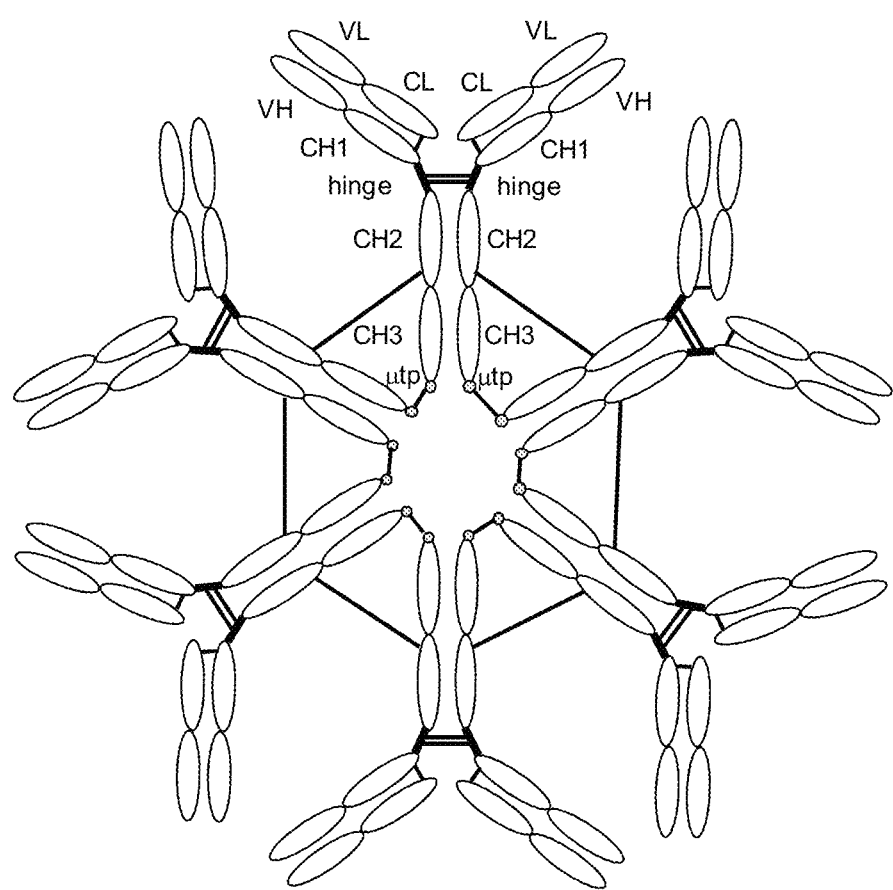
FIG. 7: An exemplary IgG antibody, having an amino acid substitution to Cys in the Fc region and carrying the μtp sequence at the end of the Fc region, in hexameric conformation. Interchain disulfide bonds are shown by linear lines. Each monomeric unit has two binding sites, each formed from a heavy chain and a light chain variable region. Six monomeric units are bonded to one another via disulfide bonding, one between the Fc regions and another between the μtp sequences of different monomeric units. The antibody shown including the valency and disulfide bonding pattern are but one embodiment of the invention provided for illustration.

The invention provides heavy chain IgG constant regions incorporating a cysteine mutation and linked at the C-terminus to a μ tailpiece (cys-μ heavy chain constant regions), and antibodies or fusion proteins incorporating the same. The heavy chain includes at least CH2 and CH3 regions. The antibodies and fusion proteins can form multivalent complexes, e.g., pentameric or hexameric structures via disulfide bond formation between mutant cysteines and between μ tailpieces. The antibodies and fusion proteins also specifically bind to protein G, which facilitates purification. The antibodies and fusion proteins optionally retain completely or partially IgG properties including pH-dependent FcRn binding, which is associated with a relatively long in vivo half-life. Depending on the isotype and subtype, the nature of the antigen and presence of additional IgG CH1 and hinge domains, IgG cys-μ heavy chain constant regions may also retain completely or partially properties of specific binding to protein A, and effector functions ADCC, CDC and opsonization. FIG. 7 shows an exemplary antibody.

The combination of IgG effector functions, relatively long half-life and ease of purification with ability to multimerize results in antibodies or fusion protein with novel combinations of properties. For example, some such antibodies or fusion protein can effectively multimerize receptors or bound ligands on the cell surface while maintaining completely or partially, or even enhancing, Fcγ-mediated properties such as ADCC, CDC, opsonization, pH-dependent FcRn binding, and the ability to bind to Protein A and Protein G relative to antibodies having an unmodified IgG isotype. The combination of properties from different isotypes offers the possibility of greater potency than conventional IgG, IgM or IgA antibodies for treatment of cancer and other diseases.

The antibody's or fusion protein's ability to multimerize also provides a format for making multi-specific complexes of antibodies and fusion proteins in which units with different specificities are held together by disulfide bonding between mutant cysteines and between μ tail pieces.

The above advantages can be achieved without in vitro manipulations other than those involved in making nucleic acid constructs for expression of the antibodies or fusion proteins incorporating cys-μ heavy chain constant regions.

II. Components of Constant Regions

The constant regions include an IgG portion and a μ tailpiece at the C-terminus. The IgG portion includes at least IgG CH2 and CH3 regions. At least one position in the CH2 and/or CH3 region is mutated to a cysteine residue. The position should support intermolecular disulfide bonding between antibody or fusion protein units, preferably without substantial impairment of desired effector functions. Cysteine residues at one or more of positions 279, 285, 287 and 309 are suitable. Preferably only one position is mutated to a cysteine to reduce the possibility of intrachain disulfide formation. However, 2, 3 or 4 residues can optionally be modified to cysteine per antibody heavy chain constant region. The CH2 and CH3 regions are responsible at least in part for FcRn binding, protein A and G binding, ADCC, CDC and opsonization. The IgG portion also preferably includes a hinge region and/or a CH1 region. The hinge region provides flexibility between the binding region and effector region of an antibody or fusion protein and contributes to efficient effector functions, such as ADCC, opsonization and CDC. The hinge region is also the site of disulfide bonds that link a pair of IgG heavy chains together. The CH1 region bonds with a light chain constant region and is generally included in formats in which a light chain with light chain constant region is present but can be omitted in fusion proteins or single-chain antibody formats in which no light chain constant region is present.

The μ tailpiece contributes together with the position mutated to cysteine in multimerizing multiple monovalent or divalent binding units into a multivalent complex. Although understanding of mechanism is not required for practice of the invention, it is believed that multimerization of antibodies or fusion proteins can occur in similar fashion as in natural IgM antibodies through the μ tailpieces of different monomers. Some multimers of IgM also contain one or more J chains bound to the μ tailpiece. In the presence of one or more J chains IgM can form a pentameric structure and in the absence of J chains can form a hexameric structure. Hexameric IgM has been reported to have stronger CDC than pentameric. Although antibodies and fusion proteins of the invention are believed to form pentameric or hexameric complexes as for IgM, other multiplicities greater or smaller may form as well or instead of pentameric and hexameric forms.

The components mentioned above are arranged from N-terminus to C-terminus in the order: IgG CH1 region (if present), IgG hinge region (if present), IgG CH2 region, IgG CH3 region, μ tailpiece.

Usually, all of the IgG regions are of the same isotype and subtype. For example, all IgG regions are either from IgG1, IgG2, IgG3 or IgG4.

Preferably, the IgG regions are human IgG. Exemplary sequences for human IgG1, IgG2, IgG3, and IgG4 heavy chains with delineation into components (CH1, hinge, CH2, CH3), μ tailpiece and a J-chain are shown in FIGS. 8 A, B, C. However, regions from other species including nonhuman primates, camelids, cartilaginous fish, mice or rats can also be used.

Reference to a human IgG or IgM region (i.e., CH1, hinge, CH2, CH3, μ tailpiece) or J-chain refers to the exemplified sequences or allotypes or isoallotypes thereof or other variant sequence having at least 90, 95, 98 or 99% sequence identity with an exemplified sequence and/or differing from the exemplified sequence by up to 1, 2, 3, 4, 5, 10 or 15 amino acid deletions, substitution or internal insertions in the case of CH1, CH2, CH3, and a J-chain, and 1, 2 or 3 deletions, substitutions or internal substitutions for IgG1, 2 or 4 hinge regions and up to 1, 2, 3, 4, 5, or 6 deletions, substitutions or internal substitutions for IgG3 hinge and up to 1 or 2 deletions, substitutions or internal substitutions for a μ tailpiece. Substitutions, if present, are preferably conservative. Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Reference to a human constant region includes a constant region with any natural allotype (including isoallotypes) or any permutation of residues occupying polymorphic positions in natural allotypes. Sequences of non-human constant regions are provided by e.g., the Swiss-Prot or Genbank databases. Reference to a non-human constant region likewise includes allotypic or isoallotypic variants, and permutations of the same, or other variants sequences differing from natural sequences. The scope of variations is defined by sequence identity and/or number of substitutions with respect to natural sequences of non-human constant regions in analogous fashion to the above description of variants with respect to human constant regions. The Eu numbering convention is used in defining corresponding positions among isotypes or different species, or defining mutated positions.

One or several amino acids at the amino or carboxy terminus of the light and/or heavy chain, such as a C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering) for increasing the half-life of an antibody. Substitution at any of positions 234, 235, 236 and/or 237 reduces affinity for Fcγ receptors, particularly FcγRI receptor (see, e.g., U.S. Pat. No. 6,624,821). Optionally, positions 234, 236 and/or 237 in human IgG2 are substituted with alanine and position 235 with glutamine. (See, e.g., U.S. Pat. No. 5,624,821.)

If a hinge region is used, part of the hinge can be replaced by a synthetic linker molecule. Such is often the case in fusion proteins in which a binding region of the fusion protein is joined to CH2 and CH3 IgG or IgA constant regions via a hinge region in which, for example, up to 10 N-terminal residues are replaced by a synthetic flexible linker. Gly-Gly-Ala-Ala (SEQ ID NO:66), Gly-Gly-Gly-Gly-Ser (SEQ ID NO:67), Leu-Ala-Ala-Ala-Ala (SEQ ID NO:68) and multimers thereof are examples of such a linker. The hinge region can also be replaced in its entirety by a synthetic linker or omitted without replacement.

With the possible exception of a synthetic linker replacing part or all of a hinge region and one or a few amino acid substitutions to enhance or suppress effector functions or FcRn binding as discussed further below, one or more cysteine mutations and linkage to a μ tailpiece at the C-terminus, and the attachment of a binding region at the N-terminus, it is preferred that constant regions contain no sequences other than the CH1, hinge, CH2, CH3, regions mentioned above. Nevertheless, other sequences, such as for example, a hexa-histidine tag, can be added but are not necessary.

A cysteine mutation means a cysteine residue occupying a position occupied by an amino acid other than cysteine in natural antibody constant region sequence (e.g., human IgG1, IgG2, IgG3 or IgG4 heavy chain shown in FIGS. 8A, B, C). V279C, H285C, A287C and L309C are preferred cysteine mutations. The wildtype residue (i.e., V, H, A or L) is the same in each of the four human isotypes. Other positions for cysteine mutation can be determined empirically as in the Examples. Criteria for selection of other positions for cysteine mutation include (i) location in the CH2 or CH3 region, (ii) exposure of its side-chain to the solvent, and/or (iii) not located at the interface of two Fc regions in the IgG structure are selected for substitution to cysteine. In brief, a construct encoding an antibody is modified or otherwise synthesized to introduce a codon at the position for the cysteine residue to be tested and μ tailpiece at the C-terminus. The construct is then transfected into suitable host cells. The supernatant of such cells is then tested for level and molecular weight of antibody produced. The molecular weight of an intact antibody (heterodimeric) is usually about 150-160 kDa. Thus, multimers of such molecular weight and in particular complexes having molecular weights of the order of 750 to 1100 indicate that a cysteine residue is effective for expression and multimerization. Such positions are preferably in the Fc region or more specifically the CH2 or CH3 region of an IgG antibody.

III. Properties of Antibodies and Fusion Proteins Incorporating Cys-μ Tailpiece

The properties of an antibody or fusion protein incorporating a heavy chain constant region as described above depend in part on the isotype, and subtype of the CH1, hinge (if present), CH2 and CH3 regions, whether the CH1 and/or hinge regions are present, and the nature of the antigen bound by the antibody or fusion protein.

Antibodies and fusion proteins incorporating the constant regions of the invention retain at least the ability to multimerize a monovalent or divalent unit to higher valency and at least one property of IgG antibodies. When CH1, hinge (if present), CH2 and CH3 are of IgG origin, the antibodies completely or partially retain at least the IgG-like properties of binding protein G, as well as capacity to specifically bind to a target antigen. pH-dependent FcRn binding may also be partially or completely retained.

Selection of isotype or subtype depends on the desired properties. As with antibodies without cys-μ heavy chain constant regions, IgG1 or IgG3 is selected if strong effector functions are desired (as is often the case against cancer cells, pathogens) and IgG2 or IgG4 is selected if weaker or no CDC, ADCC and opsonization are required (as may be the case if the mechanism is inhibition of a receptor-ligand interaction).

When the CH1 and hinge regions (if present), CH2 and CH3 regions are human IgG1, then an antibody or fusion protein incorporating a constant region of the invention has specific binding to protein A and protein G, and may have pH-dependent FcRn binding and effector functions, such as ADCC, CDC, opsonization depending on the antigen bound. Such effector functions are usually present if the antigen bound is a surface receptor (e.g., on a cell or virus). If the antigen is normally in soluble form, effector functions are not usually expressed against the soluble antigen but can be demonstrated by expressing the antigen in bound form (e.g., on a cell surface).

When the CH1 and hinge regions (if present), CH2 and CH3 regions are human IgG2, IgG4, then an antibody or fusion protein incorporating a cys-μ heavy chain constant region shows at least specific binding to protein A and protein G, and may have pH-dependent FcRn binding. Human IgG2 and IgG4 isotypes generally lack CDC. IgG4 has some ADCC and opsonization against bound antigens but less than human IgG1 or IgG3.

When the CH1 and hinge regions (if present), CH2 and CH3 regions are human IgG3, then an antibody or fusion protein incorporating a heavy chain constant region of the invention shows at least specific binding to protein G, and may have pH-dependent FcRn binding. Such an antibody or fusion protein may also show effector functions, such as ADCC, CDC, opsonization depending on whether the antigen bound is a surface antigen or soluble, as is the case for IgG1.

In antibodies or fusion proteins with constant regions of the invention in which CDC, ADCC or opsonization is present, the level of CDC, ADCC, or opsonization is sometimes the same as (within experimental error) or sometimes greater than that of an otherwise comparable antibody or fusion protein with a conventional IgG constant region.

VI. Antibody and Fusion Protein Formats

Constant regions of the invention (cys-μ heavy chain constant regions) can be incorporated into mono-specific antibodies, fusion proteins, and multi-specific complexes. For expression of a mono-specific antibody, a cys-μ heavy chain constant region can be linked to a heavy chain variable region and expressed with a light chain comprising a variable region and constant region. The heavy and light chain bind to one another via the CH1 region of the heavy chain and light chain constant region to a form a heterodimer. Two heterodimers then pair by association of hinge, CH2 and CH3 regions of the IgG portion of the heavy chain to form a tetramer unit, as is the case for a conventional antibody. Tetramer units can further multimerize by disulfide bonding between mutant cysteines and μ tailpieces of different chains.

For a mono-specific single-chain antibody, heavy and light chain variable regions are expressed as part of the same chain typically separated by a peptide spacer (see, e.g., U.S. Pat. No. 5,260,203, U.S. Pat. No. 5,869,203, U.S. Pat. No. 6,291,159). The length of the peptide spacer determines whether heavy and light chain variable regions associate intramolecularly forming a unit containing one light chain variable region intramolecularly paired to one heavy chain variable region or intermolecularly forming a tetrameric unit of two light chain variable regions and two heavy chain variable regions, each light chain variable region intermolecularly bonded to a heavy chain variable region. In either case, the units can multimerize via disulfide bonding of mutant cysteines and between tailpieces.

The cys-μ heavy chain constant regions can be used with any type of engineered antibody including chimeric, humanized, veneered or human antibodies. The antibody can be a monoclonal antibody or a genetically engineered polyclonal antibody preparation (see U.S. Pat. No. 6,986,986).

For fusion proteins, a cys-μ heavy chain constant region is expressed linked to a heterologous polypeptide. The heterologous polypeptide provides a binding region at the N-terminus of the constant region and is sometimes referred to simply as a binding region. The IgG CH1 region is not typically included in the constant region for fusion proteins. The IgG hinge region may or may not be included. In some fusion proteins, part or all of the hinge region is replaced by a synthetic linker peptide conferring flexibility between the binding portion of a fusion protein and the cys-μ heavy chain constant region.

The binding region of a fusion protein can be any of the types of binding portion used in other fusion proteins produced to date (among others). Examples of binding regions are extracellular domains of cellular receptors or their ligands or counter-receptors (e.g., TNF-alpha receptor, death family receptor, LFA3 or IL-1 receptor or Trail).

Both antibody and fusion proteins can be expressed in a multi-specific format, that is, as a complex containing antibody or fusion protein units within different target specificities. Individual specificities associate via multimerization of cys-µ heavy chain constant regions. The number of different specificities within a complex can be, for example, 2, 3, 4, 5, 6, 7, 8, 9, 10, 11 or 12. Combinations of units of different specificities can occur at two levels. In the first level, a divalent multimerization unit can contain two binding specificities as in a bispecific antibody or a heterodimeric fusion protein. In the second level of combination, multimerization units of different specificities can combine with one another via multimerization of cys-µ heavy chain constant regions. Such multimerization generates complexes of at least about five or six units.

When the two levels of combining specificities are aggregated, the present methods allow combining at least about 10 (pentamers) or 12 (hexamers) specificities in the same complex. Although in many applications, this number of specificities may be more than needed, the present methods offer an advantage in applications where fewer specificities are needed (e.g., only 2). Because of the second level at which specificities are combined, it become statistically much more likely that any complex formed includes at least one unit of each desired specificity. By contrast, when expressing a bispecific antibody by conventional methods, formation of multi-specific units may compete with formation of mono-specific units leading to a heterogeneous population of antibodies, some of which are bispecific but of which a substantial number are mono-specific.

In multi-specific formats of antibodies, the units typically contain different heavy chain variable regions. The light chain variable regions can also be different. However, it is also possible to select (e.g., using phage display) antibodies of different binding specificities having the same light chain variable region. Such antibodies can be combined in a multispecific format in which the units have different heavy chain variable regions but the same light chain variable region.

A multi-specific antibody or fusion protein can include binding specificities for an antigen on a target (e.g., a cancer cell or pathogen) and for an antigen on an effector cell (e.g., CD3 on a T-cell). Such a multi-specific complex forms a bridge between the target cell and effector cell and promotes cytotoxic or opsonization activity of the effector cell. A multi-specific antibody or fusion protein can additionally or alternatively include binding specificities for two different antigens on the same target (e.g., a cancer cell or pathogen). Such an antibody or fusion protein can have greater selective toxicity to the target cell than an antibody or fusion protein with specificity for a single antigen. Other multi-specific antibodies or fusion proteins include binding regions for both a receptor and its ligand or counter-receptor. Such antibodies or fusion proteins can exert greater inhibition than antibodies or fusion proteins binding receptor or ligand/counterreceptor alone. Any of these specificities and others can be combined in the same multi-specific complex.

VII. Exemplary Antibodies

An exemplary antibody of the invention described in Example 6 is a mouse antibody against death receptor 4. The heavy chain variable region of the antibody has the amino acid sequence shown in SEQ ID NO:23 (the signal peptide residues 1-19 can be omitted) and the light chain variable region has the amino acid sequence shown in SEQ ID NO:27 (the signal peptide of residues 1-19 can be omitted). The invention also includes other antibodies having the same three heavy chain CDRs and same three light chain CDRs (e.g., as defined by Kabat, Chothia or composite thereof) as the exemplified antibody, including humanized, chimeric or veneered forms thereof. The three heavy chain and three light chain CDRs according to Kabat or SEQ ID NOS:24-26 and 28-30 respectively. A preferred humanized antibody has a heavy chain variable region having an amino acid sequence of SEQ ID NO:31 (the signal peptide of residues 1-19 can be omitted) and a light chain variable region having an amino acid sequence of SEQ ID NO:32 (the signal peptide of residues 1-19 can be omitted). The invention also includes humanized antibodies having a mature heavy chain variable regions having at least 90, 95, 98 or 99% sequence identity with SEQ ID NO:31 (signal peptide omitted) and a mature light chain variable region having an amino acid sequence having at least 90, 95, 98 or 99% sequence identity with SEQ ID NO:32 (signal peptide omitted). Variations from the exemplified sequences are preferably at variable region framework residues not adjacent to CDRs, interacting with CDRs or binding to antigen directly (see Queen et al., U.S. Pat. Nos. 5,530,101 and 5,585,089; supra), and are preferably conservative substitutions. Nucleic acids having DNA sequences encoding the amino acid sequences described above are also provided. Preferred DNA sequences encoding the humanized antibody heavy and light chains sequences are provided by SEQ ID NOS. 33 and 34 and nucleic acids having at least 95% sequence identity therewith.

Another exemplified antibody against human death cell receptor 5 is described in Example 14. The invention further provides monoclonal antibodies comprising a mature light chain variable region comprising CDRs having amino acid sequences designated SEQ ID NO. 39, 40 and 41 respectively and comprising a mature heavy chain variable region comprising CDRs having amino acid sequences designated SEQ ID NO. 43, 44 and 45 respectively. The invention further provides monoclonal antibodies comprising a mature light chain variable region having at least 90, 95, 96, 97, 98, or 99% sequence identity to the mature variable region of SEQ ID NO. 38 (i.e., between residue 21 and the C-terminus) and a mature heavy chain variable region having at least 90, 95, 96, 97, 98 or 99% sequence identity to the mature variable region of SEQ ID NO. 42 (i.e., between residue 20 and the C-terminus). Preferably any departures from SEQ ID NO. 38 or 42 are in the variable region frameworks. Preferably such departures are conservative substitutions. The invention also includes nucleic acids encoding any of the above antibodies.

V. Genetic Engineering and Expression

Antibodies or fusion proteins including a cys-µ heavy chain constant region are produced by recombinant expression. A cys-µ heavy chain constant region is achieved by fusing a DNA segment encoding the IgG heavy chain portion in-frame with a DNA segment encoding the µ tailpiece. The IgG portion includes a cysteine mutation at one or more positions. The cysteine mutation can be introduced by mutagenesis of an existing DNA molecule (e.g., site specific or cassette) or by de novo synthesis of a DNA molecule. Preferably, the last amino acid of a CH3 exon of the IgG portion is fused in frame to the first amino acid of a µ tailpiece. The N-terminus of the segment encoding the cys-µ heavy chain constant region can be fused to a DNA segment encoding a binding region, which can be a heavy chain variable region in the case of an antibody or other binding region (e.g., an extracellular region of a cell surface receptor) in the case of fusion protein. In a single-chain antibody, a DNA construct encoding at least the light chain variable region can be fused in frame with the segment encoding the heavy chain. Alternatively, the light chain can be expressed separately, either as a different expression unit on the same vector as the heavy chain or on a separate vector. As in conventional antibody production, DNA segments encoding an antibody chain or fusion protein are typically operably linked at the N-terminus to a DNA segment encoding a signal peptide to allow secretion.

The order in which fusions of genetic elements is performed in building a construct encoding several components is not important. For example, a DNA segment encoding a heavy chain variable region can be linked to DNA encoding an IgG heavy chain constant region, which can in turn linked to DNA encoding a µ tailpiece IgM portion, or the segments encoding a cys-g heavy chain constant region can be linked to one another first. The segments can also be linked simultaneously by joining overlapping oligonucleotides encoding the respective segments in an overlapping PCR-type reaction. In practice, once an expression vector encoding a cys-µ heavy chain constant region has been produced, the same vector can be used to insert any heavy chain variable region or other binding region in the case of a fusion protein (and sometimes a light chain variable region) without recreating the DNA segment encoding the cys-µ heavy chain constant region.

Mammalian cells are a preferred host for expressing nucleotide segments encoding antibodies or fusion proteins of the invention (see Winnacker, From Genes to Clones, (VCH Publishers, NY, 1987)). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. The cells used for producing antibodies may or may not endogenously express J chains. If endogenous J chains are not expressed or are expressed at an insufficient level, host cells can be genetically modified to express J chains (i.e., by introducing a construct encoding such). However, host cells not expressing J chains can also be used. Selection of cells with or without J chains affects valency with which antibodies or fusion proteins are produced (e.g., pentamer with J chains and hexamer without). Preferably, an antibody or fusion protein of the invention is expressed from a monoclonal cell line.

Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Cells are transfected with one or more vectors encoding the antibody or fusion protein to be expressed. For a multi-chain antibody, the heavy and light chains can be expressed on the same or separate vectors. For expression of multi-specific complexes, the DNA encoding the components of the complexes (i.e., different antibodies or fusion proteins) can be on the same or different vectors.

Antibody or fusion protein chains are expressed, processed to remove signal peptides, assembled and secreted from host cells. It is believed that multimerization and association with J chains occur at least predominantly within cells so that antibodies or fusion proteins are secreted primarily as multimers, particularly multimers in which five or six units are associated via the cys-µ heavy chain constant region.

Antibodies or fusion proteins can be purified from cell culture supernatants by conventional antibody purification methods. If the cys-µ heavy chain constant region includes an IgG portion, then the purification can include a chromatography step using protein A or protein G as the affinity reagent. Conventional antibody purification procedures, such as ion exchange, hydroxyapatite chromatograph or HPLC can also be used (see generally, Scopes, Protein Purification (Springer-Verlag, NY, 1982)).

VI. Targets

Antibodies or fusion proteins incorporating a cys-µ heavy chain constant region can be made to any target molecule. The antibodies or fusion proteins are particularly useful for surface-bound target proteins (e.g., on cells or viruses) in which aggregation of the target protein induces a desired response. The desired response can be, for example, clearing of a cell or virus bearing a target, signal transduction through a receptor, e.g., inducing apoptosis or cytostasis, inhibiting a receptor binding to a ligand or counterreceptor, or internalization of an antibody or fusion protein conjugated to a toxic agent. Antibodies or fusion proteins can be made to the same targets as existing commercial antibodies or fusion proteins or can be derivatized versions of commercial antibodies or fusion proteins in which the existing constant region has been replaced by a cys-µ heavy chain constant region of the present invention. The antibodies or fusion proteins can also aggregate surface-bound antigen indirectly by binding to a target ligand bound to a surface-bound antigen.

To illustrate one possible mechanism of action, an antibody or fusion protein incorporating a cys-µ heavy chain constant region of the invention is generated with specificity to a member of the tumor necrosis factor receptor superfamily. Such receptors require trimerization for signal transduction. Because the antibody is multivalent (e.g., a pentamer or hexamer) it can multimerize antigens on the surface of tumor cells and induce apoptosis and/or growth arrest of tumor cells. Efficacy of such multivalent antibodies to treat cancer can be studied in mouse xenograft models or other appropriate animal models of cancer.

To illustrate another mechanism, an antibody or fusion protein incorporating a cys-µ heavy chain constant region is generated with specificity to an antigen expressed on the surface of immune cells, for example, B cells, T cells, monocytes, neutrophils or dendritic cells. Such an antibody can multimerize the antigen on the surface of immune cells and trigger normal or abnormal signal transduction. Alternatively, such an antibody can trigger internalization of the cell surface antigen. The function of such immune cells is enhanced or suppressed, depending on the antigen, type of cells and epitope bound, resulting in modulation of the immune system. The efficacy of such an antibody to treat immune disorders is studied in appropriate in vitro systems or animal models of an immune disorder.

To illustrate another mechanism, an antibody or fusion protein incorporating a cys-µ heavy chain constant region is generated with specificity to an antigen expressed by a pathogen, such as infectious bacteria, yeast, fungus or virus. The antibody neutralizes the infectious microorganism or virus (e.g., by ADCC, CDC, opsonization, or by inhibiting interaction between the pathogen and a cellular receptor, or by action of a toxic moiety attached to the antibody.) The efficacy of such an antibody to treat infectious diseases can be studied in appropriate in vitro systems or animal models of infection.

Targets of interest include receptors on cancer cells and their ligands or counter-receptors (e.g., CD3, CD20, CD22, CD30, CD34, CD40, CD44, CD52 CD70, CD79a, DR4 DR5, EGFR, CA-125/Muc-16, MC1 receptor, PEM antigen, gp72, EpCAM, Her-2, VEGF or VEGFR, ganglioside GD3, CEA, AFP, CTLA-4, alpha v beta 3, HLA-DR 10 beta, SK-1). Other targets of interest are autoantibodies or T-cell subsets mediating autoimmune disease. Other targets of interest are growth factor receptors (e.g., FGFR, HGFR, PDGFR, EFGR, NGFR, and VEGFR) and their ligands. Other targets are G-protein receptors and include substance K receptor, the angiotensin receptor, the α and β adrenergic receptors, the serotonin receptors, and PAF receptor. See, e.g., Gilman, Ann. Rev. Biochem. 56:625 649 (1987). Other targets include ion channels (e.g., calcium, sodium, potassium channels), muscarinic receptors, acetylcholine receptors, GABA receptors, glutamate receptors, and dopamine receptors (see Harpold, U.S. Pat. No. 5,401,629 and U.S. Pat. No. 5,436,128). Other targets are adhesion proteins such as integrins, selectins, and immunoglobulin superfamily members (see Springer, Nature 346:425 433 (1990). Osborn, Cell 62:3 (1990); Hynes, Cell 69:11 (1992)). Other targets are cytokines, such as interleukins IL-1 through about IL-37 to-date, tumor necrosis factors, interferon, and, tumor growth factor beta, colony stimulating factor (CSF) and granulocyte monocyte colony stimulating factor (GM-CSF), and cell death receptor family members, particularly DR4 or DR5. See Human Cytokines. Handbook for Basic & Clinical Research (Aggrawal et al. eds., Blackwell Scientific, Boston, Mass. 1991). Other targets are amyloidogenic peptides, such as Abeta, alpha-synuclein or prion peptide. Other targets are hormones, enzymes, and intracellular and intercellular messengers, such as, adenyl cyclase, guanyl cyclase, and phospholipase C. Target molecules can be human, mammalian or bacterial. Other targets are antigens, such as proteins, glycoproteins and carbohydrates from microbial pathogens, both viral and bacterial, and tumors. Other targets are co-stimulatory molecules, such as OX40, 4-1BB, GITR and CD27.

Some examples of commercial antibodies and their targets include alemtuzumab, CD52, rituximab, CD20, trastuzumab Her/neu, nimotuzumab, cetuximab, EGFR, bevacizumab, VEGF, palivizumab, RSV, abciximab, GpIIb/IIIa, infliximab, adalimumab, certolizumab, golimumab TNF-alpha, baciliximab, daclizumab, IL-2, omalizumab, IgE, gemtuzumab, CD33, natalizumab, VLA-4, vedolizumab alpha4beta7, belimumab, BAFF, otelixizumab, teplizumab CD3, ofatumumab, ocrelizumab CD20, epratuzumab CD22, alemtuzumumab CD52, eculizumab C5, canakimumab IL-1beta, mepolizumab IL-5, reslizumab, tocilizumab IL-6R, ustekinumab, briakinumab IL-12, 23. Examples of commercial fusion proteins include etanercept which binds TNF-alpha, alefacept (LFA3-Fc fusion which binds CD2), TACI-Fc fusion which binds BAFF and APRIL, abatacept (CTLA-4-Fc which binds CD80 and CD86), and romiplostim (a peptide analog of thrombopoietin fused to Fc). Any of the commercial antibodies or fusion protein can be modified to replace the existing heavy chain constant region with a cys-μ heavy chain constant region of the invention. Alternatively, a cys-μ constant region can be linked to other antibodies with the same target specificity (e.g., as determined by a competition assay) as any of the above commercial antibodies or fusion proteins.

VII. Immunoconjugates

Antibodies or fusion proteins can be conjugated to a toxic agent. Toxic agents can be cytotoxic or cystostatic. Some example of toxic agents include antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, camptothecins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like. A variety of radionuclides are available for the production of radioconjugated antibodies. Examples include $^{212}Bi$, $^{131}I$, $^{131}In$, $^{90}Y$, and $^{186}Re$. Conjugates of an antibody and toxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). A toxic agent can also be linked to an antibody via a linker, which may be cleavable under intracellular conditions 9US 2003-0083263, 2005-0238649 and 2005-0009751). Many of the above toxic agents are only effective or most effective when internalized within a cell. The antibodies or fusion proteins of the invention can be internalized by binding to cellular receptors, for example, crosslinking of cellular receptors can promote internalization.

VIII. Methods of Treatment and Pharmaceutical Compositions

The antibodies or fusion proteins of the invention can be used for treating cancers including those for which commercial antibodies mentioned above have been used. The methods can be used to treat solid tumors, and particularly hematological malignancies, such as leukemia (e.g., T cell large granular lymphocyte leukemia), lymphoma (Hodgkin's or Non-Hodgkin's), or multiple myeloma. Solid tumors include skin (e.g., melanoma), ovarian, endometrial, bladder, breast, rectum, colon, gastric, pancreatic, lung, thymus, kidney and brain.

The antibodies and fusion protein of the invention can also be used for suppressing various undesirable immune responses including those in which the commercial antibodies mentioned above have been used.

One category of immune disorders treatable by antibodies or fusion proteins of the invention is transplant rejection. When allogeneic cells or organs (e.g., skin, kidney, liver, heart, lung, pancreas and bone marrow) are transplanted into a host (i.e., the donor and donee are different individual from the same species), the host immune system is likely to mount an immune response to foreign antigens in the transplant (host-versus-graft disease) leading to destruction of the transplanted tissue. The antibodies of the present invention are useful, inter alia, to block alloantigen-induced immune responses in the donee.

A related use for antibodies or fusion proteins of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants.

A further situation in which immune suppression is desirable is in treatment of autoimmune diseases such as type 1 diabetes, Crohn's disease, ulcerative colitis, µltiple sclerosis, stiff man syndrome, rheumatoid arthritis, myasthenia gravis and lupus erythematosus. In these diseases, the body develops a cellular and/or humoral immune response against one of its own antigens leading to destruction of that antigen, and potentially crippling and/or fatal consequences. Autoimmune diseases are treated by administering one of the antibodies or fusion proteins of the invention.

Other immune disorders treatable by antibodies or fusion proteins of the invention, include asthma, allergies, celiac disease, psoriasis, and uveitis. Celiac disease, psoriasis and uveitis are autoimmune diseases.

The antibodies or fusion protein can also be used for treatment of pathogenic infections, such as viral, bacterial, protozoan or fungal infection. Some example of viral infections include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus. Some examples of bacterial infections include chlamydia, rickettsial bacteria, mycobacteria, staphylococci, streptococci, pneumonococci, meningococci and conococci, *klebsiella, proteus, serratia,* pseudomonas, *legionella*, diphtheria, *salmonella*, bacilli, cholera, tetanus, botulism, anthrax, plague, leptospirosis, Lymes disease bacteria, streptococci, or *neisseria*. Some examples of pathogenic fungi include *Candida, Aspergillus, Cryptococcus, Histoplasma, Pneumocystis* and Stachybotrys. Examples of protozoa include *Cryptosporidium, Giardia lamblia* and *plasmodium*.

Antibodies or fusion proteins are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody or fusion protein are 0.01-20, or 0.5-5, or 0.01-1, or 0.01-0.5 or 0.05-0.5 mg/kg body weight (e.g., 0.1, 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the antibody or fusion protein in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of chronic disorders between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

Treatment with antibodies of the invention can be combined with other treatments effective against the disorder being treated. For treatment of immune disorders, conventional treatments include mast cell degranulation inhibitors, corticosteroids, nonsteroidal anti-inflammatory drugs, and stronger anti-inflammatory drugs such as azathioprine, cyclophosphamide, leukeran, FK506 and cyclosporine. Biologic anti-inflammatory agents, such as Tysabri® (natalizumab) or Humira® (adalimumab), can also be used. When used in treating cancer, the antibodies of the invention can be combined with chemotherapy, radiation, stem cell treatment, surgery or treatment with other biologics such as Herceptin® (trastuzumab) against the HER2 antigen, Avastin® (bevacizumab) against VEGF, or antibodies to the EGF receptor, such as (Erbitux®, cetuximab), and Vectibix® (panitumumab). Chemotherapy agents include chlorambucil, cyclophosphamide or melphalan, carboplatinum, daunorubicin, doxorubicin, idarubicin, and mitoxantrone, methotrexate, fludarabine, and cytarabine, etoposide or topotecan, vincristine and vinblastine. For infections, treatment can be in combination with antibiotics, anti-virals, anti-fungal or anti-protozoan agents or the like.

XI. Other Applications

The antibodies or fusion proteins can be used for detecting their target molecule in the context of clinical diagnosis or treatment or in research. For example, the antibodies can be used to detect a cancer-related antigen as an indication a patient is suffering from an immune mediated disorder amenable to treatment. The antibodies can also be sold as research reagents for laboratory research in detecting targets and their response to various stimuli. In such uses, antibodies or fusion proteins can be labeled with fluorescent molecules, spin-labeled molecules, enzymes or radioisotopes, and can be provided in the form of kit with all the necessary reagents to perform the assay. The antibodies or fusion protein can also be used to purify their target antigens e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1

Expression Vector for Chimeric Anti-Human CD30 Monoclonal IgG Antibody

Gene cloning, mutagenesis and plasmid construction in this work was carried out with standard molecular biology techniques such as those described in Sambrook and Russel (Molecular Cloning, A Laboratory Manual, 3rd ed., 2001, Cold Spring Harbor Laboratory Press, Cold Spring Harbor, N.Y.), Kostelny et al. (Int. J. Cancer 93:556-565, 2001), Cole et al. (J. Immunol. 159:3613-3621, 1997) and Tsurushita et al. (Methods 36:69-83, 2005).

The mammalian expression vector pChSan11 (FIG. 1) for production of a mouse-human chimeric IgG1/kappa form of the mouse anti-human CD30 monoclonal antibody San11 (ChSan11) was constructed to contain the following genetic components. Proceeding clockwise from the SalI site of pChSan11 in FIG. 1, the plasmid contains the heavy chain transcription unit starting with the human cytomegalovirus (CMV) major immediate early promoter and enhancer (CMV-P in the figure) to initiate transcription of the antibody heavy chain gene. The CMV promoter is followed by an exon encoding the heavy chain variable region of the mouse anti-human CD30 monoclonal antibody San11 flanked by the SpeI and HindIII sites (San11 VH), a genomic sequence containing the human gamma-1 heavy chain constant regions including the CH1, hinge, CH2 and CH3 exons with the intervening introns, and the polyadenylation site of the human gamma-1 heavy chain gene. After the heavy chain gene sequence, the light chain transcription unit begins with the CMV promoter and enhancer (CMV-P), followed by an exon encoding the light chain variable region of the mouse anti-human CD30 monoclonal antibody San11 flanked by the NheI and EcoRI sites (San11 VL), a genomic sequence containing the human kappa chain constant region exon (Cκ) with part of the intron preceding it, and the polyadenylation site of the human kappa chain gene following the Cκ exon. The light chain gene is then followed by the SV40 early promoter (SV40-P), the puromycin N-acetyl-transferase gene (puro) for resistance to puromycin, and a segment containing the SV40 polyadenylation site (SV40-A). Finally, pChSan11 contains a part of the plasmid pUC19, comprising the bacterial origin of replication (pUC ori) and the β lactamase gene (β lactamase). Arrows in the figure indicate the orientation of transcription.

The mouse hybridoma producing the anti-human CD30 monoclonal antibody San11 was isolated at JN Biosciences using recombinant human CD30 proteins as immunogens and following standard hybridoma techniques such as the GenomONE CF EX cell fusion reagent (Cosmo Bio, Carlsbad, Calif.). The San11 VH and VL sequences were determined by standard experimental procedures such as the method described by Tsurushita et al. (supra).

The San11 VH gene placed between the SpeI and HindIII sites in pChSan11 was designed as an exon including a splice donor signal at the 3' end of the coding region. The amino acid sequence of San11 VH encoded in pChSan11, including the signal peptide, is MKCSWVIFFLMAVVT-GVNSEVQLQQSGAELVKPGASVKLSCTASGFNIKD-TYMHWVK QRPEQGLEWIGRIDPANGDTIYDPNFQG-KATITAYTSSNTAYLQLSSLTSEDTAVYYCAR GYYGSSYWYFDVWGAGTTVTVSS (SEQ ID NO:1). The mature San11 VH sequence starts at position 20 in SEQ ID NO:1.

The San11 VL gene placed between the NheI and EcoRI sites in pChSan11 was designed as an exon including a splice donor signal at the 3' end of the coding region. The amino acid sequence of San11 VL encoded in pChSan11, including the signal peptide, is MESDTLLLWVLLL-WVPGSTGDIVLTQSPASLAVSLGQRATISCRASES-VEYYGTGLMQW YQQKPGQPPKLLIYSASNVESGV-PARFTGSGSGTDFSLNIHPVEEDDIAMYFCQQSRKVP WTFGGGTKLEIKR (SEQ ID NO:2). The mature San11 VL sequence starts at position 21 in SEQ ID NO:2.

Example 2

Fc Mutants that Form Multimeric IgG Antibodies

To generate Fc mutants that form multimeric IgG antibodies, a DNA fragment encoding the 18-amino-acid-long tail piece of human μ heavy chain (μtp; also called μ tailpiece) was first fused to the 3' terminus of the gamma-1 heavy chain coding region in pChSan11 to generate pChSan11.μtp. The amino acid sequence of μtp is PTLYN-VSLVMSDTAGTCY (SEQ ID NO:3). The amino acid sequence of the heavy chain constant region encoded in pChSan11.μtp is ASTKGPSVFPLAPSSKSTSGGTAALG-CLVKDYFPEPVTVSWNSGALTSGVHTFPAVLQSS GLYSLSSVVTVPSSSLGTQTYICNVNHKPSNTKVDK-KVEPKSCDKTHTCPPCPAPELLGG PSVFLFPPKP-KDTLMISRTPEVTCVVVDVSHEDPEVKFN-WYVDGVEVHNAKTKPREEQY NSTYRVVSVLTVLHQDWLNGKEYKCKVSNKALPA-PIEKTISKAKGQPREPQVYTLPPSR DELTKNQVSLT-CLVKGFYPSDIAVEWESNGQPENNYKTTPPVLDS-DGSFFLYSKLTVDK

SRWQQGNVFSCSVMHEALHNHYTQKSLSLSPGKPT-
LYNVSLVMSDTAGTCY (SEQ ID NO:4).

An amino acid substitution to Cys was then introduced by site-directed mutagenesis at each of positions 256, 279, 283, 284, 285, 286, 287, 288, 290, 305, 307, 309, 311, 312, 433, 434 and 440 of the human gamma-1 heavy chain gene in pChSan11.μtp. Eu numbering by Kabat et al. (Sequences of Proteins of Immunological Interest, National Institutes of Health, Bethesda, Md., 1987 and 1991) is used for assigning positions of amino acids in human gamma heavy chain. Amino acid sequences of the human gamma-1 heavy chain constant regions encoded in pChSan11.μtp that carries such Cys substitution mutants are shown in SEQ ID NOs:5 to 21.

The pChSan11.μtp expression vectors carrying each of the Cys substitution mutants were individually transfected into the human embryonic kidney cell line HEK293 using Lipofectamine 2000 reagent (Invitrogen, Carlsbad, Calif.) following the manufacture's protocol. HEK293 cells were grown in DME media containing 10% fetal bovine serum (FBS; HyClone, Logan, Utah) at 37° C. in a 7.5% $CO_2$ incubator. Culture supernatants containing transiently expressed ChSan11-IgG1/kappa antibodies were fractionated by gel filtration using the AKTA Basic FPLC system with a Superose 6 10/300 GL column which has a separation range from 5 to 5,000 kilo Dalton (kDa) of globular proteins (GE Healthcare, Indianapolis, Ind.). PBS was used as elution buffer.

Presence of IgG1/kappa antibodies in each fraction was analyzed by sandwich ELISA. In a typical experiment, an ELISA plate was coated with goat anti-human gamma heavy chain polyclonal antibody in PBS (phosphate-buffered saline, pH 7.4), washed with Wash Buffer (PBS containing 0.05% Tween 20), and blocked with Blocking Buffer (PBS containing 2% Skim Milk and 0.05% Tween 20). After washing with Wash Buffer, test samples appropriately diluted in ELISA Buffer (PBS containing 1% Skim Milk and 0.025% Tween 20) were applied to the ELISA plate. An appropriate human or humanized IgG/kappa antibody was used as a standard. After incubating the ELISA plate for 1 hr at room temperature and washing with Wash Buffer, bound antibodies were detected using HRP-conjugated goat anti-human kappa chain polyclonal antibody. After incubation and washing, color development was initiated by adding ABTS substrate and stopped with 2% oxalic acid. Absorbance was read at 405 nm.

Strong ELISA signals indicating the presence of IgG1/kappa antibodies were observed in the Superose 6 fractions corresponding to roughly 1,000 kDa proteins, and thus indicating formation of multimers, with four of the seventeen Cys substitution mutants in the Fc region of the human gamma-1 chain: at position 279 from Val to Cys (V279C; SEQ ID NO:6), at position 285 from His to Cys (H285C; SEQ ID NO:9), at position 287 from Ala to Cys (A287C; SEQ ID NO:11), or at position 309 from Leu to Cys (L309C; SEQ ID NO:16). Strong ELISA signals were also observed with these four Cys substitution mutants in the fractions corresponding to roughly 150 kDa proteins. ChSan11 showed strong ELISA signals only in the fractions corresponding to roughly 150 kDa proteins.

These four Cys substitution mutants (V279C, H285C, A287C and L309C) were further studied for the ability to produce multimeric IgG antibodies. The pChSan11.μtp expression vectors carrying an amino acid substitution to Cys at position 279 (V279C; SEQ ID NO:6), at position 285 (H285C; SEQ ID NO:9), at position 287 (A287C; SEQ ID NO:11) and at position 309 (L309C; SEQ ID NO:16) were designated pChSan11.V279-Fcμtp, pChSan11.H285-Fcμtp, pChSan11.A287-Fcμtp, and pChSan11.L309-Fcμtp, respectively.

Example 3

Expression and Purification of Anti-CD30 IgG Antibodies

The expression vector pChSan11 was introduced into the chromosome of a mouse myeloma cell line NS0 (European Collection of Animal Cell Cultures, Salisbury, Wiltshire, UK) to obtain a cell line stably producing ChSan11 IgG1/kappa antibody. NS0 cells were grown in DME medium containing 10% FBS at 37° C. in a 7.5% $CO_2$ incubator. Stable transfection into NS0 was carried out by electroporation as described in Bebbington et al. (Bio/Technology 10: 169-175, 1992). Before transfection, each expression vector was linearized using FspI. In a typical experiment, approximately $10^7$ cells were transfected with 20 μg of linearized plasmid, suspended in DME medium containing 10% FBS, and plated into several 96-well plates. After 48 hr, selection media (DME medium containing 10% FBS, HT media supplement (Sigma, St. Louis, Mo.), 0.25 mg/ml xanthine and 1 μg/ml mycophenolic acid) was applied. Approximately 10 days after the initiation of selection, culture supernatants of transfectants were assayed for antibody by ELISA as described above. NS0 stable transfectants producing ChSan11 were adapted to growth in serum-free media using Hybridoma SFM (Invitrogen, Carlsbad, Calif.) and cultured in a roller bottle until the cell viability became less than 50%. After centrifugation and filtration, culture supernatant was stored at 4° C.

The expression vectors pChSan11.V279-Fcμtp, pChSan11.H285-Fcμtp, pChSan11.A287-Fcμtp and pChSan11.L309-Fcμtp were individually introduced into the chromosome of a Chinese hamster ovary cell line CHO—S (Invitrogen), which does not express J chains, to obtain cell lines stably producing IgG1/kappa antibodies ChSan11.V279-Fcμtp, ChSan11.H285-Fcμtp, ChSan11.A287-Fcμtp and ChSan11.L309-Fcμtp, respectively. CHO—S cells were grown in SFM4-CHO media (HyClone) at 37° C. in a 7.5% $CO_2$ incubator. Stable transfection into CHO—S was carried out by electroporation. Before transfection, each expression vector was linearized using FspI. In a typical experiment, approximately $10^7$ cells were transfected with 20 μg of linearized plasmid, suspended in SFM4-CHO, and plated into several 96-well plates after appropriate dilutions of cells. After 48 hr, puromycin was added for selection of stable transfectants. Approximately two weeks after the initiation of selection, culture supernatants of transfectants were assayed for antibody production. Expression of antibodies was measured by sandwich ELISA as described above. CHO—S stable transfectants producing each of ChSan11.V279-Fcμtp, ChSan11.H285-Fcμtp, ChSan11.A287-Fcμtp and ChSan11.L309-Fcμtp were expanded in SFM4-CHO until the cell viability became less than 50%. After centrifugation and filtration, culture supernatants were stored at 4° C.

For antibody purification, culture supernatants were loaded onto a Protein A column (HiTrap MABSelect SuRe, GE Healthcare, Piscataway, N.J.). The column was washed with PBS before the antibody was eluted with 0.1 M glycine-HCl (pH 3.0). Buffer of all eluted antibodies was neutralized with 1 M Tris-HCl (pH 8) and then changed to PBS by dialysis. Antibody concentration was determined by measuring absorbance at 280 nm (1 mg/ml=1.4 OD).

Example 4

Characterization of Multimeric Anti-CD30 Antibodies

Purified ChSan11, ChSan11.V279-Fcμtp, ChSan11.H285-Fcμtp, ChSan11.A287-Fcμtp and ChSan11.L309-Fcμtp IgG1/kappa antibodies were characterized by SDS-PAGE according to standard procedures. Analysis under reducing conditions indicated that each of these antibodies is comprised of a heavy chain with a molecular weight of approximately 53 kDa (for ChSan11) or 56 kDa (for ChSan11.V279-Fcμtp, ChSan11.H285-Fcμtp, ChSan11.A287-Fcμtp and ChSan11.L309-Fcμtp) and a light chain with a molecular weight of approximately 27 kDa. The increase in the molecular weight of the heavy chain of ChSan11.V279-Fcμtp, ChSan11.H285-Fcμtp, ChSan11.A287-Fcμtp and ChSan11.L309-Fcμtp, when compared to the heavy chain of ChSan11, is attributed to the addition of the 18-amino-acid-long μtp and the presence of a carbohydrate attachment site in the μtp sequence.

The molecular size of purified ChSan11, ChSan11.V279-Fcμtp, ChSan11.H285-Fcμtp, ChSan11.A287-Fcμtp and ChSan11.L309-Fcμtp antibodies in the native form was analyzed by gel filtration using a Superose 6 10/300 GL column. A single dominant peak was observed for ChSan11 at 15.4 ml of elution. When compared to the elution pattern of molecular size markers, the size of ChSan11 in the native form was estimated to be approximately 150 kDa, which is consistent with the size of a monomeric human IgG1 antibody composed of two heavy and two light chains. Each of ChSan11.V279-Fcμtp, ChSan11.H285-Fcμtp, ChSan11.A287-Fcμtp and ChSan11.L309-Fcμtp antibodies showed two major peaks in the elution pattern; one peak corresponding to monomeric IgG antibodies with the estimated molecular weight of approximately 170 kDa and another peak corresponding to multimeric IgG antibodies with the molecular weight of roughly 1,000 kD.

The multimeric form of ChSan11.V279-Fcμtp, ChSan11.H285-Fcμtp, ChSan11.A287-Fcμtp and ChSan11.L309-Fcμtp antibodies (ChSan11.V279-Fcμtp multimer, ChSan11.H285-Fcμtp multimer, ChSan11.A287-Fcμtp multimer, and ChSan11.L309-Fcμtp multimer, respectively) corresponding to approximately 1,000 kDa of molecular weight in the Superose 6 gel filtration fractions were tested for their ability to induce cell growth arrest of the human T cell lymphoma cell line Karpas 299. Cross-linking of CD30 proteins on the cell surface by treatment with a mixture of a mouse monoclonal anti-CD30 IgG antibody and a polyclonal anti-mouse IgG antibody caused cytostasis of Karpas 299 (Wahl et al., Cancer Res. 62:3736-3742, 2002). To investigate the ability of the multimeric anti-CD30 IgG antibodies to cross-link CD30 proteins, $2 \times 10^5$ Karpas 299 cells were incubated in 0.2 ml of RPMI-1640 media containing 10% FBS in a 96-well plate in the presence of 2 μg/ml of each of ChSan11-IgG1, ChSan11.V279-Fcμtp multimer, ChSan11.H285-Fcμtp multimer, ChSan11.A287-Fcμtp multimer, and ChSan11.L309-Fcμtp multimer. After 5-day incubation, Karpas 299 cells were incubated with the tetrazolium salt WST-8 (Dojindo Molecular Technologies, Rockville, Md.) and absorbance at 450 nm, which is indicative of the level of dehydrogenase activity and therefore directly related to viable cell number, was measured. Percent cell growth was calculated by normalizing the absorbance value in the presence of test antibodies to the value with no antibody. The absorbance value when no cells were present was used as the background. The growth level of Karpas 299 cells was 106% with ChSan11, 41% with ChSan11.V279-Fcμtp multimer, 39% with ChSan11.H285-Fcμtp multimer, 43% with ChSan11.A287-Fcμtp multimer, and 38% with ChSan11.L309-Fcμtp multimer. Thus, each of ChSan11.V279-Fcμtp multimer, ChSan11.H285-Fcμtp multimer, ChSan11.A287-Fcμtp multimer, and ChSan11.L309-Fcμtp multimer was shown to function as a multivalent antibody that can cross-link CD30 molecules on the cell surface and induce growth arrest of Karpas 299 cells.

Example 5

Humanization of Mouse Anti-CD30 Monoclonal Antibody San11

Humanization of San11 VH and VL is carried out by the procedure described by Tsurushita et al. (supra). A gene encoding humanized San11 VH is synthesized as an exon including a splice donor signal at the 3' end of the coding region, an SpeI site at the 5' end of the fragment, and a HindIII site at the 3' end of the fragment. A gene encoding humanized San11 VL is synthesized as an exon including a splice donor signal at the 3' end of the coding region, a NheI site at the 5' end of the fragment, and an EcoRI site at the 3' end of the fragment. A mammalian expression vector for production of humanized anti-human CD30 monoclonal IgG1/kappa antibody is constructed by modifying pChSan11 as follows: (1) the San11 VH gene is replaced with the humanized VH gene between the SpeI and HindIII sites, and (2) the San11 VL gene is replaced with the humanized San11 VL gene between the NheI and EcoRI sites. For expression of multimeric humanized San11 antibodies, the humanized San11 VH and VL genes are substituted for the ChSan11 VH and VL genes, respectively, at the corresponding sites in pChSan11.V279-Fcμtp, pChSan11.H285-Fcμtp, pChSan11.A287-Fcμtp, or pChSan11.L309-Fcμtp. The resulting expression vectors are individually introduced into the chromosome of a eukaryotic cell. Stable transfectants are expanded in appropriate culture media. Multimeric humanized anti-CD30 IgG antibodies are purified as described in Example 3.

Example 6

Vectors for Expression of Multimeric Anti-DR4 Antibodies

The mouse hybridoma producing anti-human death receptor 4 (DR4; also called Apo2, TRAIL receptor 1 and TNFRSF10A) monoclonal IgG1/lambda antibody YON007 was generated at JN Biosciences (Mountain View, Calif.) using the extracellular region of human DR4 fused to the Fc region of human gamma-1 heavy chain (DR4-Fc) (SEQ ID NO:22) as immunogens and following standard hybridoma techniques.

The amino acid sequence of YON007 VH was determined by standard experimental procedures such as the method described by Tsurushita et al. (supra). The amino acid sequence of YON007 VH, including the signal peptide sequence, is MNRLTSSLLLLIVPAYVLSQVTLKES-GPGILQPSQTLSLTCSFSGFSLSTSGMGVSWIRQPS GKGLEWLAHIYWDDDKRYNPSLKSRLKISKDTSSN-QVFLKITSVDTADTATYYCTRRGE YGNFDYWGQGT- TLTVSS (SEQ ID NO:23). The mature YON007 VH starts at position 20 in SEQ ID NO:23. The CDR1, CDR2 and CDR3 amino acid sequences of YON007 VH based on the definition of Kabat et al. (supra) are TSGMG (SEQ ID NO:24), HIYWDDDKRYNPSLK (SEQ ID NO:25) and RGEYGNFDY (SEQ ID NO:26), respectively.

Similarly, the amino acid sequence of YON007 VL was determined. The amino acid sequence of YON007 VL, including the signal peptide sequence, is MAWISLILSLLALSSGAISQAVVTQESALTTSPGETVTLTCRSSSGAVTTSNFANWVQEK PDHLFTGLIGGTNNRAPGVPARFSGSLIGDKAALTITGAQTEDEAIYFCALWYSNHWVF GGGTKLTVL (SEQ ID NO:27). The mature YON007 VL starts at position 20 in SEQ ID NO:27. The CDR1, CDR2 and CDR3 amino acid sequences of YON007 VL based on the definition of Kabat et al. (supra) are RSSSGAVTTSNFAN (SEQ ID NO:28), GTNNRAP (SEQ ID NO:29) and ALWYSNHWV (SEQ ID NO:30), respectively.

Humanization of YON007 VH and VL was carried out by the procedure described by Tsurushita et al. (supra). The amino acid sequence of humanized YON007 (HuYON007) VH, including the signal peptide, is MNRLTSSLLLLIVPAYVLSQVTLRESGPALVKPTQTLTLTCTFSGFSLSTSGMGVSWIRQP PGKALEWLAHIYWDDDKRYNPSLKSRLTISKDTSKNQVVLTMTNMDPVDTATYYCTRR GEYGNFDYWGQGTLVTVSS (SEQ ID NO:31). The mature HuYON007 VH sequence starts at position 20 in SEQ ID NO:31. The amino acid sequence of HuYON007 VL is MAWISLILSLLALSSGAISQTVVTQEPSFSVSPGGTVTLTCRSSSGAVTTSNFANWVQQTP GQAPRGLIGGTNNRAPGVPDRFSGSLLGNKAALTITGAQADDESDYYCALWYSNHWVF GGGTKLTVL (SEQ ID NO:32). The mature HuYON007 VL sequence starts at position 20 in SEQ ID NO:32.

A gene encoding HuYON007 VH (SEQ ID NO:33) was synthesized as an exon including a splice donor signal at the 3' end of the coding region, an SpeI site at the 5' end of the fragment, and a HindIII site at the 3' end of the fragment. A gene encoding HuYON007 VL (SEQ ID NO:34) was synthesized as an exon including a splice donor signal at the 3' end of the coding region, a NheI site at the 5' end of the fragment, and an EcoRI site at the 3' end of the fragment.

Figure 2:
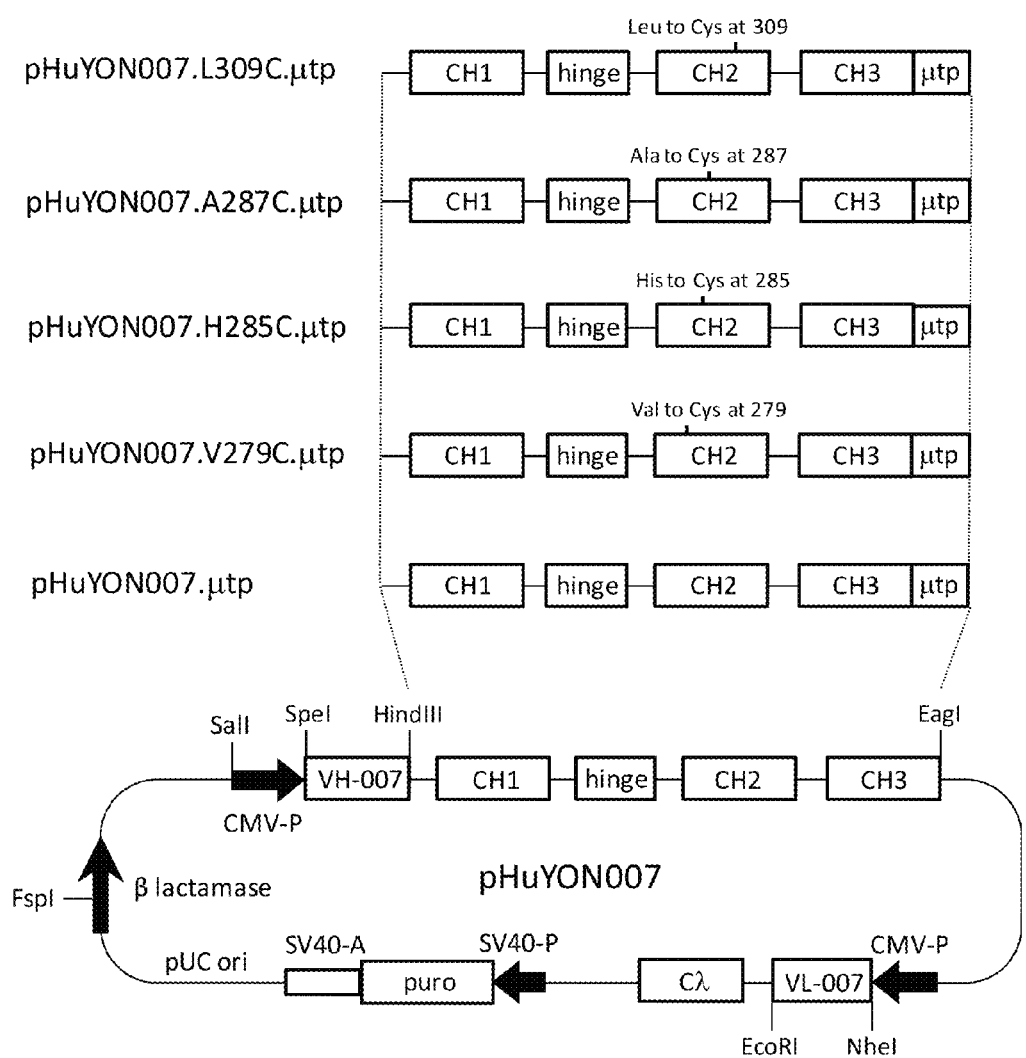
FIG. 2: Schematic structure of expression vectors for YON007 antibodies.

The mammalian expression vector pHuYON007 (FIG. 2) for production of a humanized anti-human DR4 monoclonal IgG1/lambda antibody HuYON007 was constructed by modifying pChSan11 as follows: (1) the San11 VH gene was replaced with the HuYON007 VH gene (SEQ ID NO: 33; shown as "VH-007" in FIG. 2) between the SpeI and HindIII sites, (2) the San11 VL gene was replaced with the HuYON007 VL gene (SEQ ID NO:34; shown as "VL-007" in FIG. 2) between the NheI and EcoRI sites, and (3) the Cκ-coding exon was replaced with the exon encoding the human lambda-2 constant region (Cλ). The schematic structure of pHuYON007 is shown in FIG. 2. Arrows in the figure indicate the orientation of transcription.

The amino acid sequence of the mature heavy chain encoded in pHuYON007 is QVTLRESGPALVKPTQTLTLTCTFSGFSLSTSGMGVSWIRQPPGKALEWLAHIYWDDDK RYNPSLKSRLTISKDTSKNQVVLTMTNMDPVDTATYYCTRRGEYGNFDYW GQGTLVT VSSASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCDKTHTCPPCPAPEL LGGPSVFLFPPKPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKGQPREPQVYTLP PSRDELTKNQVSLTCLVKGFYPSDIAVEWESNGQPENNYKTTPPVLDSDGSFFLYSKLTV DKSRWQQGNVFSCSVMHEALHNHYTQKSLSLSPGK (SEQ ID NO:35).

The amino acid sequence of the mature light chain encoded in pHuYON007 is QTVVTQEPSFSVSPGGTVTLTCRSSSGAVTTSNFANWVQQTPGQAPRGLIGGTNNRAPG VPDRFSGSILGNKAALTITGAQADDESDYYCALWYSNHWVFGGGTKLTVLGQPKAAPS VTLFPPSSEELQANKATLVCLISDFYPGAVTVAWKADSSPVKAGVETTTPSKQSNNKYA ASSYLSLTPEQWKSHRSYSCQVTHEGSTVEKTVAPTECS (SEQ ID NO:36).

For expression of multimeric HuYON007 IgG antibodies, a DNA fragment encoding the 18-amino-acid-long tail piece of human μ heavy chain (μtp) (SEQ ID NO:3) was fused to the 3' terminus of the gamma-1 heavy chain in pHuYON007 to generate pHuYON007.μtp. The amino acid sequence of the heavy chain constant region encoded in pHuYON007.μtp is same as that encoded in pChSan11.μtp (SEQ ID NO: 4)

The expression vector pHuYON007.μtp was further modified by introducing an amino acid substitution to Cys at each of positions 279, 285, 287 and 309 in the heavy chain gene to generate pHuYON007.V279-Fcμtp, pHuYON007.H285-Fcμtp, pHuYON007.A287-Fcμtp and pHuYON007.L309-Fcμtp, respectively. In pHuYON007.V279-Fcμtp, Val at position 279 in the Fc region was substituted to Cys. The amino acid sequence of the heavy chain constant region encoded in pHuYON007.V279-Fcμtp is same as that encoded in pChSan11.V279-Fcμtp (SEQ ID NO: 6). In pHuYON007.H285-Fcμtp, His at position 285 was substituted to Cys. The amino acid sequence of the heavy chain constant region encoded in pHuYON007.H285-Fcμtp is same as that encoded in pChSan11.H285-Fcμtp (SEQ ID NO:9). In pHuYON007.A287-Fcμtp, Ala at position 287 was substituted to Cys. The amino acid sequence of the heavy chain constant region encoded in pHuYON007.A287-Fcμtp is same as that encoded by pChSan11.A287-Fcμtp (SEQ ID NO:11). In pHuYON007.L309-Fcμtp, Leu at position 309 was substituted to Cys. The amino acid sequence of the heavy chain constant region encoded in pHuYON007.L309-Fcμtp is same as that encoded in pChSan11.L309-Fcμtp (SEQ ID NO:16).

The same amino acid sequence is encoded by the light chain gene in each of pHuYON007, pHuYON007.μtp, pHuYON007.V279-Fcμtp, pHuYON007.H285-Fcμtp, pHuYON007.A287-Fcμtp and pHuYON007.L309-Fcμtp.

The schematic structure of the expression vectors pHuYON007.μtp, pHuYON007.V279-Fcμtp, pHuYON007.H285-Fcμtp, pHuYON007.A287-Fcμtp and pHuYON007.L309-Fcμtp is shown in FIG. 2.

Example 7

Expression and Purification of Anti-DR4 IgG1 Antibodies

The expression vectors pHuYON007, pHuYON007.V279-Fcμtp, pHuYON007.H285-Fcμtp, pHuYON007.A287-Fcμtp and pHuYON007.L309-Fcμtp were individually introduced into the chromosome of a Chinese hamster ovary cell line CHO—S (Invitrogen) to obtain cell lines stably producing humanized IgG1/lambda antibodies HuYON007, HuYON007.V279-Fcμtp, HuYON007.H285-Fcµtp, HuYON007.A287-Fcµtp, and HuYON007.L309-Fcµtp, respectively. Stable transfection into CHO—S, selection and expansion of CHO—S stable transfectants, and antibody purification were carried out as described above.

Purified HuYON007, HuYON007.V279-Fcµtp, YON007.H285-Fcµtp, HuYON007.A287-Fcµtp and HuYON007.L309-Fcµtp IgG1/lambda antibodies were characterized by SDS-PAGE according to standard procedures. Analysis under reducing conditions indicated that each of these antibodies is comprised of a heavy chain with a molecular weight of approximately 51 kDa (for HuYON007) or 54 kDa (for HuYON007.V279-Fcµtp, HuYON007.H285-Fcµtp, HuYON007.A287-Fcµtp and HuYON007.L309-Fcµtp) and a light chain with a molecular weight of approximately 27 kDa. The increase in the molecular weight of the heavy chain of HuYON007.V279-Fcµtp, HuYON007.H285-Fcµtp, HuYON007.A287-Fcµtp and HuYON007.L309-Fcµtp, when compared to the heavy chain of HuYON007, is attributed to the addition of the 18-amino-acid-long µtp and the presence of a carbohydrate attachment site in µtp.

The molecular size of HuYON007, HuYON007.V279-Fcµtp, HuYON007.H285-Fcµtp, HuYON007.A287-Fcµtp and HuYON007.L309-Fcµtp IgG1/lambda antibodies in the native form was analyzed by gel filtration using a Superose 6 10/300 GL as described above. A single dominant peak was observed for HuYON007 at 15.4 ml of elution (FIG. 3B). When compared to the elution pattern of molecular size markers (FIG. 3A), the size of HuYON007 in the native form was estimated to be approximately 150 kDa, which is consistent with the size of a monomeric human IgG1 antibody composed of two heavy and two light chains. Each of HuYON007.V279-Fcµtp (FIG. 3C), HuYON007.H285-Fcµtp (FIG. 3D), HuYON007.A287-Fcµtp (FIG. 3E) and HuYON007.L309-Fcµtp (FIG. 3F) showed two major peaks in the elution pattern. The fraction eluted at ~15 ml corresponds to monomeric IgG antibodies with the estimated molecular weight of approximately 180 kDa, while the fraction eluted at ~11 ml correspond to multimeric IgG antibodies with the molecular weight of roughly 1,000 kDa, which corresponds to a pentamer or hexamer of IgG antibodies.

Multimeric antibodies were separated from monomeric antibodies by gel filtration using a Superose 6 column for HuYON007.V279-Fcµtp, HuYON007.H285-Fcµtp, HuYON007.A287-Fcµtp, and HuYON007.L309-Fcµtp. The gel filtration pattern of fractionated multimeric antibodies is shown in FIG. 4A for HuYON007.V279-Fcµtp (HuYON007.V279-Fcµtp multimer), in FIG. 4C for HuYON007.H285-Fcµtp (HuYON007.H285-Fcµtp multimer), in FIG. 4E for HuYON007.A287-Fcµtp (HuYON007.A287-Fcµtp multimer), and in FIG. 4G for HuYON007.L309-Fcµtp (HuYON007.L309-Fcµtp multimer). Each of HuYON007.V279-Fcµtp, HuYON007.H285-Fcµtp, HuYON007.A287-Fcµtp, and HuYON007.L309-Fcµtp multimers shows a single dominant peak at ~11 ml of elution, which corresponds to ~1,000 kDa molecules. The gel filtration pattern of fractionated monomeric antibodies is shown in FIG. 4B for HuYON007.V279-Fcµtp (HuYON007.V279-Fcµtp monomer), in FIG. 4D for HuYON007.H285-Fcµtp (HuYON007.H285-Fcµtp monomer), in FIG. 4F for HuYON007.A287-Fcµtp (HuYON007.A287-Fcµtp monomer), and in FIG. 4H for HuYON007.L309-Fcµtp (HuYON007.L309-Fcµtp monomer). Each of these four monomers shows a single dominant peak at ~15 ml of elution, which corresponds to ~180 kDa molecules.

Example 8

Apoptosis of Ramos Cells by HuYON007 Antibodies

The human Burkitt's lymphoma cell line Ramos expresses DR4 on the cell surface (Daniel et al. Blood: 110:4037-4046, 2007). Multimerization of DR4 by cross-linking is known to induce apoptosis of cells (Griffith et al. J. Immunol. 162:2597-2605, 1999).

Ramos cells (CRL-1596; ATCC, Manassas, Va.) were grown in DME media containing 10% FBS. To assess the ability of HuYON007.V279-Fcµtp, HuYON007.H285-Fcµtp, HuYON007.A287-Fcµtp and HuYON007.L309-Fcµtp IgG1 antibodies to induce apoptosis of Ramos cells via cross-linking of DR4 on the surface, each of purified HuYON007.V279-Fcµtp multimer, HuYON007.H285-Fcµtp multimer, HuYON007.A287-Fcµtp multimer, and HuYON007.L309-Fcµtp multimer was incubated with Ramos cells in duplicate wells at a final concentration of 100 ng/ml, 20 ng/ml, 4 ng/ml, 0.8 ng/ml, 0.16 ng/ml or 0.032 ng/ml. Each of the purified HuYON007.V279-Fcµtp monomer, HuYON007.H285-Fcµtp monomer, HuYON007.A287-Fcµtp monomer, and HuYON007.L309-Fcµtp monomer was also incubated with Ramos cells at a final concentration of 100 ng/ml, 20 ng/ml, 4 ng/ml, 0.8 ng/ml, 0.16 ng/ml or 0.032 ng/ml. After overnight incubation at 37° C. in a 7.5% $CO_2$ incubator, cell viability was measured with alamarBlue (Invitrogen) according to the manufacturer's protocol. Percent cell viability was calculated by normalizing the absorbance value in the presence of test antibodies to that in the absence of test antibodies. The absorbance value with no cells was used as background.

Each of HuYON007.V279-Fcµtp multimer, HuYON007.H285-Fcµtp multimer, HuYON007.A287-Fcµtp multimer, and HuYON007.L309-Fcµtp multimer efficiently induced apoptosis of Ramos cells (FIGS. 5A, 5B, 5C and 5D, respectively). At 100 ng/ml of antibody, nearly 100% cell killing was achieved with each of these four multimers. In contrast, each of HuYON007.V279-Fcµtp monomer, HuYON007.H285-Fcµtp monomer, HuYON007.A287-Fcµtp monomer, and HuYON007.L309-Fcµtp monomer did not induce efficient apoptosis of Ramos cells (FIGS. 5A, 5B, 5C and 5D, respectively). In the presence of 100 ng/ml of antibody, cell viability was 80% for HuYON007.V279-Fcµtp monomer, 91% for HuYON007.H285-Fcµtp monomer, 83% for HuYON007.A287-Fcµtp monomer, and 92% for HuYON007.L309-Fcµtp monomer.

Example 9

Apoptosis of Colo-205 Cells by HuYON007 Antibodies

Multimerization of DR4 on the cell surface by cross-linking is known to induce apoptosis of the human colon cancer cell line Colo1-205 (Chuntharapai et al., J. Immunol. 166:4891-4898, 2001). To assess the ability of HuYON007.V279-Fcµtp, YON007.H285-Fcµtp, HuYON007.A287-Fcµtp, and HuYON007.L309-Fcµtp IgG1 antibodies to induce apoptosis of Colo-205 cells (CCL-222; ATCC) via cross-linking of DR4 on the surface, each of purified HuYON007.V279-Fcμtp multimer, YON007.H285-Fcμtp multimer, HuYON007.A287-Fcμtp multimer, and HuYON007.L309-Fcμtp IgG1 multimer was incubated with Colo-205 cells in duplicate wells at a final concentration of 100 ng/ml, 20 ng/ml, 4 ng/ml, 0.8 ng/ml, 0.16 ng/ml or 0.032 ng/ml. Each of the purified HuYON007.V279-Fcμtp monomer, HuYON007.H285-Fcμtp monomer, HuYON007.A287-Fcμtp monomer, and HuYON007.L309-Fcμtp monomer was also incubated with Colo-205 cells at a final concentration of 100 ng/ml, 20 ng/ml, 4 ng/ml, 0.8 ng/ml, 0.16 ng/ml or 0.032 ng/ml. After overnight incubation at 37° C. in a 7.5% $CO_2$ incubator, cell viability was measured with alamarBlue (Invitrogen) according to the manufacturer's protocol. Percent cell viability was calculated by normalizing the absorbance value in the presence of test antibodies to that in the absence of test antibodies. The absorbance value with no cells was used as background.

Each of HuYON007.V279-Fcμtp multimer, HuYON007.H285-Fcμtp multimer, HuYON007.A287-Fcμtp multimer, and HuYON007.L309-Fcμtp multimer efficiently induced apoptosis of Colo-205 cells in a dose-dependent manner (FIGS. 6A, 6B, 6C and 6D, respectively). At 100 ng/ml of antibody, the viability of Colo-205 cells was less than 35% with each of the four multimers. In contrast, with each of HuYON007.V279-Fcμtp monomer, HuYON007.H285-Fcμtp monomer, HuYON007.A287-Fcμtp monomer, and HuYON007.L309-Fcμtp monomer, no reduction of the viability was observed even at the highest antibody concentration tested (100 ng/ml) (FIGS. 6A, 6B, 6C and 6D, respectively).

Example 10

Combination of a Multimeric IgG Antibody and a Chemotherapy Agent for Treatment of Cancer Cells Apoptosis of the human myeloma cell line RPMI 8226, which expresses DR4 on the cell surface, can be induced by an agonist anti-DR4 antibody (Locklin et al., Leukemina 21:805-812, 2007). To assess the ability of HuYON007.V279-Fcμtp multimer to induce apoptosis of RPMI 8226 cells via cross-linking of DR4 on the surface, RPMI 8226 cells (CCL-155, ATCC) were cultured in the absence or presence of HuYON007.V279-Fcμtp multimer. In addition, the synergy of HuYON007.V279-Fcμtp multimer with bortezomib, a chemotherapy agent approved for treatment of multiple myeloma, was examined for killing of RPMI 8226 cells.

RPMI 8226 cells were grown in RPMI-1640 media containing 10% FBS for 24 hr in the presence of (i) 4.1 ng/ml of HuYON007.V279-Fcμtp multimer, (ii) 2.5 ng/ml of bortezomib, (iii) 4.1 ng/ml of HuYON007.V279-Fcμtp multimer and 2.5 ng/ml of bortezomib, or (iv) no additives for 100% viability control. The viability of RPMI 8226 cells, measured using CellTiter-Glo Luminescent Cell Viability Assay (Promega, Madison, Wis.), was 43% for treatment with HuYON007.V279-Fcμtp multimer alone, 49% with bortezomib alone, and 9.5% with a mixture of HuYON007.V279-Fcμtp multimer and bortezomib. While each of HuYON007.V279-Fcμtp multimer bortezomib induced cell death of RPMI 8226 cells, the killing activity was much higher when HuYON007.V279-Fcμtp multimer and bortezomib were used together.

Example 11

Mouse Systemic Xenograft Model with Ramos Cells

Therapeutic efficacy of HuYON007.V279-Fcμtp multimer was evaluated using a mouse systemic xenograft model with Ramos cells. For tumor development, CB17 SCID female mice were inoculated on Day 0 with $5 \times 10^6$ Ramos cells intravenously into the tail vein. HuYON007 IgG1 (0.5 mg/kg), HuYON007.V279-Fcμtp multimer (0.5 mg/kg), or PBS was administered intravenously to the tumor-bearing mice on Days 7, 10, 14, 17, 21, 24, 28, and 31. The mice were monitored daily for morbidity and mortality. Mice were euthanized when hind leg paralysis was observed or more than 20% of body weight was lost. The study was terminated on Day 45.

Figure 9:
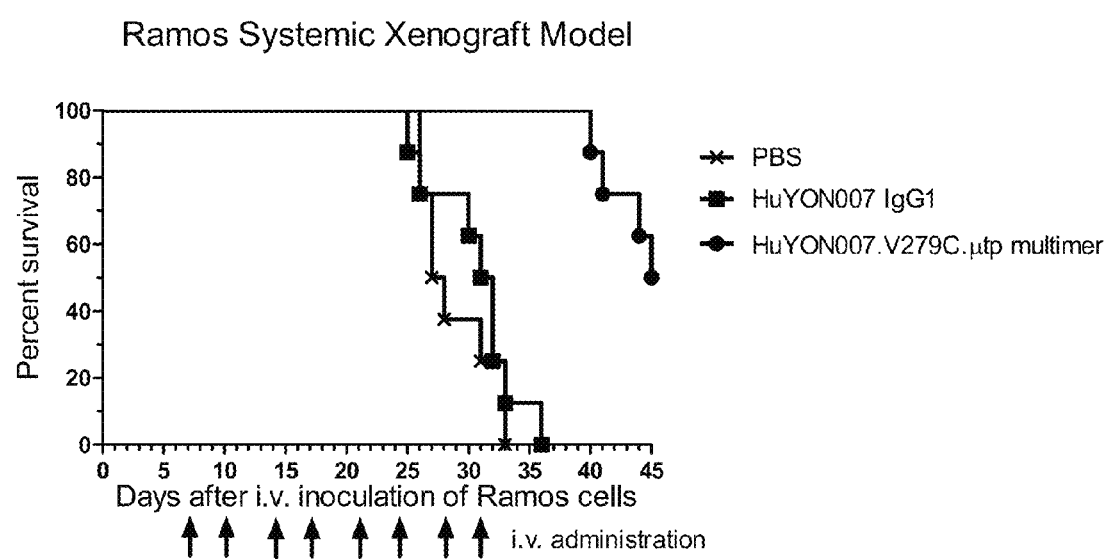
FIG. 9: Survival data of Ramos-bearing CB17 SCID mice treated with HuYON007.V279-Fcμtp multimer or HuYON007 IgG1.

Mice survival was plotted using the Kaplan-Meier method (FIG. 9) and analyzed for significance using the Mantel-Cox test. The mean survival time was 27.5 days for the PBS-treated group, 31.5 days for the group treated with HuYON007 IgG1, and 45 days for the group treated with HuYON007.V279-Fcμtp multimer. The P value between the PBS-treated and HuYON007.V279-Fcμtp multimer-treated groups was less than 0.0001. The P value between the HuYON007 IgG1-treated and HuYON007.V279-Fcμtp multimer-treated groups was less than 0.0001. HuYON007.V279-Fcμtp multimer was significantly more efficacious than HuYON007 IgG1 as therapeutics in the mouse systemic xenograft treatment model with Ramos cells.

Example 12

Multimeric Anti-CD40 Agonist Antibody

CD40, a member of the TNF receptor superfamily, is expressed on the surface of various types of cells including antigen-presenting cells and functions as a costimulatory molecule in the immune system. CD40 ligand, also called CD40L and CD154, is a member of the TNF superfamily. CD154 is primarily expressed on the surface of activated T cells and also exists as a soluble trimer. Ligation of CD40 on antigen-presenting cells through interaction with CD154 triggers immune responses, such as antibody production, tumor killing, and elimination of virally infected cells (for review, see Grewal and Flavell, Annu Rev. Immunol. 16:111-135, 1998).

The human Burkitt's B lymphoma cell line Ramos expresses CD40 on the surface (Henriquez et al., J. Immunol. 162:3298-3307, 1999). Ligation of CD40 on the surface of Ramos cells with soluble trimeric CD154 is known to induce activation of NF-κB and elevated expression of CD54 and CD95 (Henriquez et al., supra).

To examine the effect of monomeric and multimeric anti-CD40 IgG antibodies on activation of Ramos cells, expression vectors for recombinant chimeric anti-CD40 antibodies were generated. The coding region of the VH gene of a mouse anti-human CD40 monoclonal antibody was converted to an exon including a signal peptide-coding sequence, a splice donor signal, and flanking SpeI and HindIII sites. Likewise, the VL gene of the same mouse anti-CD40 monoclonal antibody was converted to an exon including a signal peptide-coding sequence, a splice donor signal, and flanking NheI and EcoRI sites. The SpeI-HindIII fragment carrying the VH exon and the NheI-EcoRI fragment carrying the VL exon derived from the mouse anti- CD40 monoclonal antibody were introduced to the corresponding sites of pChSan11 (FIG. 1). The resultant expression vector was named pChACD40. Similarly, the same VH and VL fragments were introduced into pChSan11.V279-Fcµtp (FIG. 1) to generate pChACD40.V279-Fcµtp. The overall structure of pChACD40 and pChACD40.V279-Fcµtp is essentially identical to that of pChSan11 and pChSan11.V279-Fcµtp, respectively, except that the VH and VL genes are different. Mouse-human chimeric antibodies expressed from each of pChACD40 and pChACD40.V279-Fcµtp bound specifically to human CD40.

Generation of CHO—S stable transfectants with pChACD40.V279-Fcµtp and pChACD40 for production of ChACD40.V279-Fcµtp multimer and ChACD40 IgG1, respectively, was carried out as described in Example 7. Each of ChACD40.V279-Fcµtp multimer and ChACD40 IgG1 antibodies was purified from culture supernatants of the corresponding CHO—S stable transfectants as described in Example 7. The molecular size of ChACD40.V279-Fcµtp multimer and ChACD40 IgG1 was analyzed by gel filtration using a Superose 6 10/300 GL as described above. A single dominant peak corresponding to approximately 1,000 kDa was observed for ChACD40.V279-Fcµtp multimer. ChACD40 IgG1 showed a single major peak corresponding to roughly 150 kDa.

Ramos cells were grown with 1 µg/ml of ChSan11 IgG1, ChACD40 IgG1 or ChACD40.V279-Fcµtp multimer in RPMI-1640 media containing 10% FBS at 37° C. in a 7.5% $CO_2$ incubator. After 48 hr incubation, cells were stained with PE-labeled mouse anti-CD95 monoclonal antibody and analyzed by flow cytometry. Mean channel fluorescence (MCF) of Ramos cells grown with ChSan11 IgG1, which does not bind to Ramos cells, was 9.2. MCF values of cells grown with ChACD40 IgG1 and ChACD40.V279-Fcµtp multimer were 19.8 and 180.7, respectively. ChACD40.V279-Fcµtp multimer induced up-regulation of CD95 in Ramos cells much more efficiently than ChACD40 IgG1 did. Thus, the ChACD40.V279-Fcµtp multimer was a much more efficient agonist than was ChACD40 IgG1.

Administration of anti-CD40 antibodies in the multimeric IgG form of this invention, such as ChACD40.V279-Fcµtp, will be an effective way to activate the immune system for treatment of cancer and infectious diseases (Li and Ravetch, Science 333:1030-1034, 2011; Antunes et al., J. Biomed. Biotechnol. 2012:464532, 2012; Capece et al., J. Biomed. Biotechnol. 2012:926321, 2012).

Example 13

Activation of the Immune System with a Multimeric IgG Antibody Binding to a Costimulatory Molecule Activation of T cells in adaptive immune responses requires two distinctive signaling events. The first signal is provided by the engagement of T cell receptors with MHC molecules on antigen-presenting cells in an antigen-dependent manner. The second signal is provided by the interaction of costimulatory molecules with their ligands between T cells and antigen-presenting cells. Induction of intracellular signaling via cross-linking of costimulatory molecules, such as OX40, 4-1BB, GITR and CD27, by their ligands or agonist antibodies has been shown to trigger immune responses efficiently (for review, see McNamara et al., J. Clin. Invest. 118:376-386, 2008; Sharpe, Immunol. Rev. 229:5-11, 2009; Capece et al., supra; Antunes et al., supra; Gao et al., Trends Immunol. 34:90-98, 2013). Cross-linking of costimulatory molecules by multimeric IgG antibodies of this invention will offer a potent mechanism for activation of the immune system.

VH and VL genes of a non-human, humanized or human monoclonal antibody against a co-stimulatory molecule, such as OX40, 4-1BB, GITR and CD27, are cloned into an appropriate vector, such as pChSan11.H285-Fcµtp or pHuYON007.V279-Fcµtp, for expression in the multimeric IgG form of this invention. The resulting multimeric IgG antibody is expressed in an appropriate cell and purified by affinity chromatography as described above. Activation of the immune system by such multimeric IgG antibody is tested in appropriate cell-based assays or animals, for example, immunodeficient mice having engraftment of human immune cells (humanized mice; Schultz et al., Nat. Rev. Immunol. 12:786-798, 2012). The therapeutic activity of such multimeric IgG antibody is examined in appropriate animal disease models such as humanized mice harboring cancer or pathogens (Brehm et al., Curr. Opin. Endocrinol. Diabetes Obes. 17:120-125, 2010; Dranoff et al., Nat. Rev. Immunol. 12:61-66, 2012; Strowig et al., Drug Discovery Today: Disease Models 9:e11-e16, 2012; Akkina, Virology 435:14-28, 2013).

Example 14

Bispecific Multimeric IgG Antibodies

Figure 10:
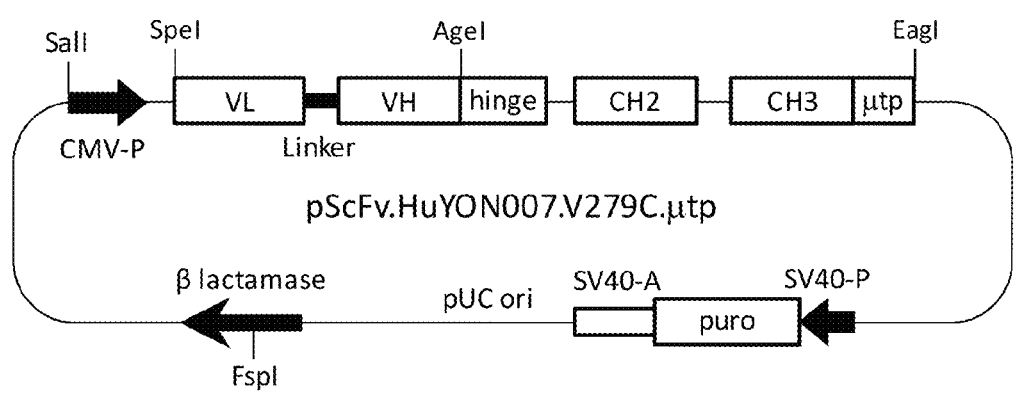
FIG. 10: Schematic map of a vector for expression of HuYON007.V279-Fcμtp in the single chain Fv form.

For expression of HuYON007.V279-Fcµtp multimer in the single chain Fv (scFv) format (Ahmad et al. Clin. Dev. Immunol. 2012:980250, 2012), the expression vector pHuYON007.V279-Fcµtp was modified by first removing the light chain gene and then replacing the VH, CH1 and hinge exons with a synthetic exon encoding, from 5' to 3', HuYON007 VL including its signal peptide, a flexible polypeptide linker, mature HuYON007 VH, a flexible polypeptide linker and then human gamma-1 heavy chain hinge region. The schematic structure of the resultant expression vector pScFv.HuYON007.V279-Fcµtp is shown in FIG. 10. Single-chain Fv antibodies expressed from pScFv.HuYON007.V279-Fcµtp (SEQ ID NO:37) bound specifically to human DR4.

The VL and VH regions of the humanized anti-human death receptor 5 (DR5; also called TRAIL receptor 2, TNFRSF10B, CD262) monoclonal antibody HuGOH729S, which had been generated at JN Biosciences using standard hybridoma and humanization technologies, were cloned into the corresponding positions in pScFv.HuYON007.V279-Fcµtp as described above to generate another scFv expression vector pScFv.HuGOH729S.V279-Fcµtp. The amino acid sequence of HuGOH729S VL, including the signal peptide sequence, is MESQIQAFVFVFLWLS-GVDGDIQMTQSPSSLSASVGDRVTITCKASQDVN-TAAAWYQQ KPGKAPKLLIYWASTRHTGVPSRF-SGSGSGTDYTLTISSLQPEDFATYYCQQHYSTPYTF GQGTKLEIK (SEQ ID NO:38). The mature HuGOH729S VL starts at position 21 in SEQ ID NO:38. The CDR1, CDR2 and CDR3 amino acid sequences of HuGOH729S VL based on the definition of Kabat et al. (supra) are KASQD-VNTAAA (SEQ ID NO:39), WASTRHT (SEQ ID NO:40) and QQHYSTPYT (SEQ ID NO:41), respectively. The amino acid sequence of HuGOH729S VH, including the signal peptide sequence, is MEWCWVFLFLLSVTAGVH-SQVQLVQSGAEVKKPGASVKVSCKASGYTFTDYIIH-WVR QAPGQGLEWIGWFYPGNNNIKSNEK-FKDRVTLTADTSTSTVYMELSSLRSEDTAVYYC ARNEDNYGNFFGYWGQGTLVTVSS (SEQ ID NO:42).

The mature HuGOH729S VH starts at position 20 in SEQ ID NO:42. The CDR1, CDR2 and CDR3 amino acid sequences of HuGOH729S VH based on the definition of Kabat et al. (supra) are DYIIH (SEQ ID NO:43), WFYPGNNNIKSNEKFKD (SEQ ID NO:44) and NED-NYGNFFGY (SEQ ID NO:45), respectively. Single-chain Fv antibodies expressed from pScFv.HuGOH729S.V279-Fcµtp (SEQ ID NO:46) bound specifically to human DR5.

The expression vectors pScFv.HuYON007.V279-Fcµtp and pScFv.HuGOH729S.V279-Fcµtp were either individually or together transfected into HEK293 cells for antibody expression as described above. Transiently expressed antibodies in culture supernatants of HEK293 cells were tested for simultaneous binding to DR4 and DR5 by ELISA.

Wells of a microtiter plate were coated with recombinant human DR4 extracellular region fused at the C-terminus to the Fc region of human γ1 chain (DR4-Fc; SEQ ID NO:22). After blocking the wells with Block Buffer, appropriately diluted culture supernatants of HEK293 cells were applied to the wells and incubated for 1 hr at room temperature. After washing wells with Wash Buffer, recombinant human DR5 extracellular region fused at the C-terminus to the human λ2 constant region (DR5-Cλ; SEQ ID NO:47) in ELISA Buffer was applied to the wells. A cysteine residue at the second location from the carboxyl terminus in the human λ2 constant region was changed to a serine residue in DR5-Cλ. After incubating the ELISA plate for 30 min at room temperature and washing the wells with Wash Buffer, bound DR5-Cλ was detected by HRP-conjugated goat anti-human λ chain polyclonal antibody. Color development was initiated by adding ABTS substrate and stopped with 2% oxalic acid. Absorbance was read at 405 nm.

Culture supernatants of HEK293 cells transfected with either pScFv.HuYON007.V279-Fcµtp or pScFv.HuGOH729S.V279-Fcµtp showed no signal when compared to the culture supernatant of untransfected HEK293 cells. When pScFv.HuYON007.V279-Fcµtp and pScFv.HuGOH729S.V279-Fcµtp were cotransfected into HEK293 cells, the culture supernatant showed a strong signal in this format of ELISA, indicating the presence of bispecific multimeric antibodies that can bind simultaneously to DR4-Fc coated on the ELISA plate and DR5-Cλ in solution.

Various pairs of antibodies against cell surface antigens are expressed in the bispecific multimeric IgG form as shown above. Such bispecific multimeric IgG antibodies are incubated with normal, malignant or pathogen-infected cells. Changes of antibody-treated cells, such as apoptosis, cytostasis, enhanced growth, differentiation, morphological changes, alteration of protein expression, and modulation of intracellular signal transduction, are analyzed to identify bispecific multimeric IgG antibodies that are useful as reagents, diagnostics or therapeutics.

Example 15

Screening of Functional Multimeric Antibodies

An antibody display library, such as a scFv phage display library, is generated using VH and VL genes derived from a nave or immunized animal or using synthetic VH and VL genes and then subjected to enrichment of antibodies that bind to the surface of normal, malignant or pathogen-infected cells following standard procedures (Kretzschmar et al., Current Opinion Biotechnol. 13:598-602, 2002; Dufner et al., Treads Biotechnol. 24:523-529, 2006; Shibasaki et al., Recent Patents Biotechnol. 3:19-37, 2009; Mannocci et al., Chem. Commun. 47:12747-12753, 2011; Geyer et al., Antibody Methods and Protocols, Methods Mol. Biol. Vol. 901, Chapter 2, 2012). A mixture of VH-VL gene pairs in the enriched library is transferred to a vector for expression of multimeric IgG antibodies of this invention, for example, pScFv.HuYON007.V279-Fcµtp or pHuYON007.V279-Fcµtp, to generate a secondary antibody library.

Each vector in the secondary antibody library is transfected into cells for expression of a monospecific multimeric IgG antibody binding to a cell surface antigen. Alternatively, each vector in the secondary antibody library is cotransfected into cells with another vector encoding a multimeric IgG antibody binding to a known cell surface antigen for production of a bispecific multimeric IgG antibody binding to two distinct cell surface antigens. Such expressed monospecific and bispecific multimeric antibodies are individually incubated with normal, malignant or pathogen-infected cells. Changes of antibody-treated cells, such as apoptosis, cytostasis, enhanced growth, differentiation, morphological changes, alteration of protein expression, and modulation of intracellular signal transduction, are monitored. Therapeutic efficacy of such monospecific and bispecific multimeric IgG antibodies binding to cell surface antigens are further examined in appropriate animal models as described above.

What is claimed is:

1. An antibody comprising IgG hinge, CH2 and CH3 regions in N- to C-terminal order, wherein position 279, 285 or 287 by EU numbering in the CH2 region is mutated to a cysteine residue and the CH3 region is linked to a μ tailpiece at its C-terminus, wherein units of the antibody can multimerize via disulfide bonding between cysteines at the mutated position in different units and between μ tailpieces in different units.

2. The antibody of claim 1 further comprising an IgG CH1 region N-terminal to the hinge.

3. The antibody of claim 1 that specifically binds to a Death Receptor family protein.

4. The antibody of claim 3, wherein the Death Receptor family protein is DR4 or DR5.

5. The antibody of claim 1, further comprising a human IgG CH1 region N-terminal to the hinge.

6. The antibody of claim 1 that specifically binds to a TNF receptor family protein.

7. An antibody comprising human IgG1, IgG2 or IgG4 hinge, CH2 and CH3 regions in N- to C-terminal order, wherein position 279, 285 or 287 by EU numbering in the CH2 region is mutated to a cysteine residue and the CH3 region is linked to a μ tailpiece at its C-terminus, wherein units of the antibody can multimerize via disulfide bonding between cysteines at the mutated position in different units and between μ tailpieces in different units.

8. The antibody of claim 1, which is a single-chain antibody comprising a single-chain Fv linked to the heavy chain constant region.

9. The antibody of claim 8, which is a component of a multi-specific antibody comprising a plurality of the single-chain antibodies, wherein the single chain Fvs of the plurality have different VH regions, and the plurality of single-chain antibodies are complexed in the multispecific antibody via disulfide bonding between cysteines at the mutated position in different units and between μ tailpieces in different units.

10. The antibody of claim 9, wherein the single chain Fvs have the same VL region.

11. The antibody of claim 1, which specifically binds protein G, specifically binds protein A, exhibits ADCC, CDC and/or opsonization.

12. The antibody of claim 11, wherein a CH1 region, if present, and the hinge region, and CH2 and CH3 regions are human IgG1 regions, and the antibody specifically binds protein G, and specifically binds protein A.

13. The antibody of claim 12 that exhibits ADCC, CDC and opsonizaton.

14. The antibody of claim 1, wherein a CH1 region if present, and the hinge, CH2 and CH3 regions are human IgG2 or IgG4 regions and the antibody specifically binds protein G and specifically binds protein A.

15. The antibody of claim 1 that is a component of a multispecific complex comprising antibodies complexed by disulfide bonding between the cysteines at the mutated position and between μ tailpieces in different units.

16. The antibody of claim 1, wherein the antibody is a humanized, chimeric, veneered or human antibody.

17. The antibody of claim 1 that specifically binds the extracellular domain of a receptor.

18. The antibody of claim 17, which is an antibody that specifically binds to CD79a, CD30, DR5 or DR4.

19. The antibody of claim 17, which is an antibody that specifically binds to CD40, OX40, 4-1BB, GITR or CD27.

20. A pharmaceutical composition comprising an antibody as defined in claim 1 and a pharmaceutically acceptable carrier.

21. An antibody comprising human IgG hinge, CH2 and CH3 regions in N- to C-terminal order, wherein position 309 in the CH2 region is mutated to a cysteine residue and position 310 is histidine and the CH3 region is linked to a μ tailpiece at its C-terminus, wherein units of the antibody can multimerize via disulfide bonding between cysteines at the mutated position in different units and between μ tailpieces in different units.

* * * * *

SEQUENCE LISTING

```
<160> NUMBER OF SEQ ID NOS: 68

<210> SEQ ID NO 1
<211> LENGTH: 140
<212> TYPE: PRT
<213> ORGANISM: Artificial Sequence
<220> FEATURE:
<223> OTHER INFORMATION: Synthesized

<400> SEQUENCE: 1

Met Lys Cys Ser Trp Val Ile Phe Phe Leu Met Ala Val Val Thr Gly
 1               5                  10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
```

```
            35                  40                  45
Lys Asp Thr Tyr Met His Trp Val Lys Gln Arg Pro Glu Gln Gly Leu
 50                  55                  60

Glu Trp Ile Gly Arg Ile Asp Pro Ala Asn Gly Asp Thr Ile Tyr Asp
 65                  70                  75                  80

Pro Asn Phe Gln Gly Lys Ala Thr Ile Thr Ala Tyr Thr Ser Ser Asn
                 85                  90                  95

Thr Ala Tyr Leu Gln Leu Ser Ser Leu Thr Ser Glu Asp Thr Ala Val
            100                 105                 110

Tyr Tyr Cys Ala Arg Gly Tyr Tyr Gly Ser Ser Tyr Trp Tyr Phe Asp
        115                 120                 125

Val Trp Gly Ala Gly Thr Thr Val Thr Val Ser Ser
130                 135                 140

<210> SEQ ID NO 2
<211> LENGTH: 132
<212> TYPE: PRT
<213> ORGANISM: Artificial Sequence
<220> FEATURE:
<223> OTHER INFORMATION: Synthesized

<400> SEQUENCE: 2

Met Glu Ser Asp Thr Leu Leu Leu Trp Val Leu Leu Leu Trp Val Pro
  1               5                  10                  15

Gly Ser Thr Gly Asp Ile Val Leu Thr Gln Ser Pro Ala Ser Leu Ala
                 20                  25                  30

Val Ser Leu Gly Gln Arg Ala Thr Ile Ser Cys Arg Ala Ser Glu Ser
             35                  40                  45

Val Glu Tyr Tyr Gly Thr Gly Leu Met Gln Trp Tyr Gln Gln Lys Pro
 50                  55                  60

Gly Gln Pro Pro Lys Leu Leu Ile Tyr Ser Ala Ser Asn Val Glu Ser
 65                  70                  75                  80

Gly Val Pro Ala Arg Phe Thr Gly Ser Gly Ser Gly Thr Asp Phe Ser
                 85                  90                  95

Leu Asn Ile His Pro Val Glu Glu Asp Asp Ile Ala Met Tyr Phe Cys
            100                 105                 110

Gln Gln Ser Arg Lys Val Pro Trp Thr Phe Gly Gly Gly Thr Lys Leu
        115                 120                 125

Glu Ile Lys Arg
130

<210> SEQ ID NO 3
<211> LENGTH: 18
<212> TYPE: PRT
<213> ORGANISM: Artificial Sequence
<220> FEATURE:
<223> OTHER INFORMATION: Synthesized

<400> SEQUENCE: 3

Pro Thr Leu Tyr Asn Val Ser Leu Val Met Ser Asp Thr Ala Gly Thr
  1               5                  10                  15

Cys Tyr

<210> SEQ ID NO 4
<211> LENGTH: 348
<212> TYPE: PRT
<213> ORGANISM: Artificial Sequence
<220> FEATURE:
<223> OTHER INFORMATION: Synthesized
```

<400> SEQUENCE: 4

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
            340                 345
```

<210> SEQ ID NO 5
<211> LENGTH: 348
<212> TYPE: PRT
<213> ORGANISM: Artificial Sequence
<220> FEATURE:
<223> OTHER INFORMATION: Synthesized

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Cys Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
            340                 345

<210> SEQ ID NO 6
<211> LENGTH: 348
<212> TYPE: PRT
<213> ORGANISM: Artificial Sequence
<220> FEATURE:
<223> OTHER INFORMATION: Synthesized

<400> SEQUENCE: 6

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
     130                 135                 140

Val Val Val Asp Val Ser His Glu Asp Pro Glu Val Lys Phe Asn Trp
145                 150                 155                 160

Tyr Cys Asp Gly Val Glu Val His Asn Ala Lys Thr Lys Pro Arg Glu
                 165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
         195                 200                 205

Lys Ala Leu Pro Ala Pro Ile Glu Lys Thr Ile Ser Lys Ala Lys Gly
     210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                 245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
         275                 280                 285

Leu Tyr Ser Lys Leu Thr Val Asp Lys Ser Arg Trp Gln Gln Gly Asn
     290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                 325                 330                 335

Ser Leu Val Met Ser Asp Thr Ala Gly Thr Cys Tyr
            340                 345

<210> SEQ ID NO 7
<211> LENGTH: 348
<212> TYPE: PRT
<213> ORGANISM: Artificial Sequence
<220> FEATURE:
<223> OTHER INFORMATION: Synthesized

<400> SEQUENCE: 7

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Cys Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
            340                 345

<210> SEQ ID NO 8
<211> LENGTH: 348
<212> TYPE: PRT
<213> ORGANISM: Artificial Sequence
<220> FEATURE:
<223> OTHER INFORMATION: Synthesized

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Cys His Asn Ala Lys Thr Lys Pro Arg Glu
                    165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                    325                 330                 335

Ser Leu Val Met Ser Asp Thr Ala Gly Thr Cys Tyr
            340                 345

<210> SEQ ID NO 9
<211> LENGTH: 348
<212> TYPE: PRT
<213> ORGANISM: Artificial Sequence
<220> FEATURE:
<223> OTHER INFORMATION: Synthesized

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val Cys Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
            340                 345

<210> SEQ ID NO 10
<211> LENGTH: 348
<212> TYPE: PRT
<213> ORGANISM: Artificial Sequence
<220> FEATURE:
<223> OTHER INFORMATION: Synthesized

<400> SEQUENCE: 10

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Cys Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
            340                 345

<210> SEQ ID NO 11
<211> LENGTH: 348
<212> TYPE: PRT
<213> ORGANISM: Artificial Sequence
<220> FEATURE:
<223> OTHER INFORMATION: Synthesized

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Cys Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
            340                 345

<210> SEQ ID NO 12
<211> LENGTH: 348
<212> TYPE: PRT
<213> ORGANISM: Artificial Sequence
<220> FEATURE:
<223> OTHER INFORMATION: Synthesized

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Cys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
            325                 330                 335

Ser Leu Val Met Ser Asp Thr Ala Gly Thr Cys Tyr
            340                 345

<210> SEQ ID NO 13
<211> LENGTH: 348
<212> TYPE: PRT
<213> ORGANISM: Artificial Sequence
<220> FEATURE:
<223> OTHER INFORMATION: Synthesized

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

```
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Cys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys Pro Thr Leu Tyr Asn Val
                325                 330                 335
Ser Leu Val Met Ser Asp Thr Ala Gly Thr Cys Tyr
            340                 345
```

<210> SEQ ID NO 14
<211> LENGTH: 348
<212> TYPE: PRT
<213> ORGANISM: Artificial Sequence
<220> FEATURE:
<223> OTHER INFORMATION: Synthesized

<400> SEQUENCE: 14

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Cys Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
            325                 330                 335

Ser Leu Val Met Ser Asp Thr Ala Gly Thr Cys Tyr
            340                 345

<210> SEQ ID NO 15
<211> LENGTH: 348
<212> TYPE: PRT
<213> ORGANISM: Artificial Sequence
<220> FEATURE:
<223> OTHER INFORMATION: Synthesized

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Cys Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
            340                 345

<210> SEQ ID NO 16
<211> LENGTH: 348
<212> TYPE: PRT
<213> ORGANISM: Artificial Sequence
<220> FEATURE:
<223> OTHER INFORMATION: Synthesized

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Cys
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
                340                 345

<210> SEQ ID NO 17
<211> LENGTH: 348
<212> TYPE: PRT
<213> ORGANISM: Artificial Sequence
<220> FEATURE:
<223> OTHER INFORMATION: Synthesized

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Cys Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
            340                 345

<210> SEQ ID NO 18
<211> LENGTH: 348
<212> TYPE: PRT
<213> ORGANISM: Artificial Sequence
<220> FEATURE:
<223> OTHER INFORMATION: Synthesized

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Cys Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
                340                 345

<210> SEQ ID NO 19
<211> LENGTH: 348
<212> TYPE: PRT
<213> ORGANISM: Artificial Sequence
<220> FEATURE:
<223> OTHER INFORMATION: Synthesized

<400> SEQUENCE: 19

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Cys
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
                340                 345

<210> SEQ ID NO 20
<211> LENGTH: 348
<212> TYPE: PRT
<213> ORGANISM: Artificial Sequence
<220> FEATURE:
<223> OTHER INFORMATION: Synthesized

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Cys Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Pro Thr Leu Tyr Asn Val
                325                 330                 335

Ser Leu Val Met Ser Asp Thr Ala Gly Thr Cys Tyr
            340                 345

<210> SEQ ID NO 21
<211> LENGTH: 348
<212> TYPE: PRT
<213> ORGANISM: Artificial Sequence
<220> FEATURE:
<223> OTHER INFORMATION: Synthesized

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Cys Leu Ser Leu Ser Pro Gly Lys Pro Thr Leu Tyr Asn Val
            325                 330                 335

Ser Leu Val Met Ser Asp Thr Ala Gly Thr Cys Tyr
            340                 345

<210> SEQ ID NO 22
<211> LENGTH: 452
<212> TYPE: PRT
<213> ORGANISM: Artificial Sequence
<220> FEATURE:
<223> OTHER INFORMATION: Synthesized

<400> SEQUENCE: 22

Ala Ser Gly Thr Glu Ala Ala Ala Thr Pro Ser Lys Val Trp Gly
 1               5                  10                  15

Ser Ser Ala Gly Arg Ile Glu Pro Arg Gly Gly Arg Gly Ala Leu
            20                  25                  30

Pro Thr Ser Met Gly Gln His Gly Pro Ser Ala Arg Ala Arg Ala Gly
        35                  40                  45

Arg Ala Pro Gly Pro Arg Pro Ala Arg Glu Ala Ser Pro Arg Leu Arg
 50                  55                  60

Val His Lys Thr Phe Lys Phe Val Val Gly Val Leu Leu Gln Val
65                  70                  75                  80

Val Pro Ser Ser Ala Ala Thr Ile Lys Leu His Asp Gln Ser Ile Gly
            85                  90                  95

Thr Gln Gln Trp Glu His Ser Pro Leu Gly Glu Leu Cys Pro Pro Gly
        100                 105                 110

Ser His Arg Ser Glu His Pro Gly Ala Cys Asn Arg Cys Thr Glu Gly
        115                 120                 125

Val Gly Tyr Thr Asn Ala Ser Asn Asn Leu Phe Ala Cys Leu Pro Cys
    130                 135                 140

Thr Ala Cys Lys Ser Asp Glu Glu Arg Ser Pro Cys Thr Thr Thr
145                 150                 155                 160

Arg Asn Thr Ala Cys Gln Cys Lys Pro Gly Thr Phe Arg Asn Asp Asn
                165                 170                 175

Ser Ala Glu Met Cys Arg Lys Cys Ser Thr Gly Cys Pro Arg Gly Met
            180                 185                 190

Val Lys Val Lys Asp Cys Thr Pro Trp Ser Asp Ile Glu Cys Val His
        195                 200                 205

Lys Glu Ser Gly Asn Gly His Asn Thr Gly Gly Gly Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

-continued

```
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 23
<211> LENGTH: 138
<212> TYPE: PRT
<213> ORGANISM: Artificial Sequence
<220> FEATURE:
<223> OTHER INFORMATION: Synthesized

<400> SEQUENCE: 23

Met Asn Arg Leu Thr Ser Ser Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Lys Arg Tyr
65                  70                  75                  80

Asn Pro Ser Leu Lys Ser Arg Leu Lys Ile Ser Lys Asp Thr Ser Ser
                85                  90                  95

Asn Gln Val Phe Leu Lys Ile Thr Ser Val Asp Thr Ala Asp Thr Ala
            100                 105                 110

Thr Tyr Tyr Cys Thr Arg Arg Gly Glu Tyr Gly Asn Phe Asp Tyr Trp
        115                 120                 125

Gly Gln Gly Thr Thr Leu Thr Val Ser Ser
    130                 135

<210> SEQ ID NO 24
<211> LENGTH: 5
<212> TYPE: PRT
<213> ORGANISM: Artificial Sequence
<220> FEATURE:
```

```
<223> OTHER INFORMATION: Synthesized

<400> SEQUENCE: 24

Thr Ser Gly Met Gly
  1               5

<210> SEQ ID NO 25
<211> LENGTH: 16
<212> TYPE: PRT
<213> ORGANISM: Artificial Sequence
<220> FEATURE:
<223> OTHER INFORMATION: Synthesized

<400> SEQUENCE: 25

His Ile Tyr Trp Asp Asp Lys Arg Tyr Asn Pro Ser Leu Lys Ser
  1               5                  10                  15

<210> SEQ ID NO 26
<211> LENGTH: 9
<212> TYPE: PRT
<213> ORGANISM: Artificial Sequence
<220> FEATURE:
<223> OTHER INFORMATION: Synthesized

<400> SEQUENCE: 26

Arg Gly Glu Tyr Gly Asn Phe Asp Tyr
  1               5

<210> SEQ ID NO 27
<211> LENGTH: 128
<212> TYPE: PRT
<213> ORGANISM: Artificial Sequence
<220> FEATURE:
<223> OTHER INFORMATION: Synthesized

<400> SEQUENCE: 27

Met Ala Trp Ile Ser Leu Ile Leu Ser Leu Leu Ala Leu Ser Ser Gly
  1               5                  10                  15

Ala Ile Ser Gln Ala Val Val Thr Gln Glu Ser Ala Leu Thr Thr Ser
                 20                  25                  30

Pro Gly Glu Thr Val Thr Leu Thr Cys Arg Ser Ser Ser Gly Ala Val
             35                  40                  45

Thr Thr Ser Asn Phe Ala Asn Trp Val Gln Glu Lys Pro Asp His Leu
         50                  55                  60

Phe Thr Gly Leu Ile Gly Gly Thr Asn Asn Arg Ala Pro Gly Val Pro
 65                  70                  75                  80

Ala Arg Phe Ser Gly Ser Leu Ile Gly Asp Lys Ala Ala Leu Thr Ile
                 85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Thr Val Leu
        115                 120                 125

<210> SEQ ID NO 28
<211> LENGTH: 14
<212> TYPE: PRT
<213> ORGANISM: Artificial Sequence
<220> FEATURE:
<223> OTHER INFORMATION: Synthesized

<400> SEQUENCE: 28

Arg Ser Ser Ser Gly Ala Val Thr Thr Ser Asn Phe Ala Asn
  1               5                  10
```

<210> SEQ ID NO 29
<211> LENGTH: 7
<212> TYPE: PRT
<213> ORGANISM: Artificial Sequence
<220> FEATURE:
<223> OTHER INFORMATION: Synthesized

<400> SEQUENCE: 29

Gly Thr Asn Asn Arg Ala Pro
1               5

<210> SEQ ID NO 30
<211> LENGTH: 9
<212> TYPE: PRT
<213> ORGANISM: Artificial Sequence
<220> FEATURE:
<223> OTHER INFORMATION: Synthesized

<400> SEQUENCE: 30

Ala Leu Trp Tyr Ser Asn His Trp Val
1               5

<210> SEQ ID NO 31
<211> LENGTH: 138
<212> TYPE: PRT
<213> ORGANISM: Artificial Sequence
<220> FEATURE:
<223> OTHER INFORMATION: Synthesized

<400> SEQUENCE: 31

Met Asn Arg Leu Thr Ser Ser Leu Leu Leu Ile Val Pro Ala Tyr
1               5                   10                  15

Val Leu Ser Gln Val Thr Leu Arg Glu Ser Gly Pro Ala Leu Val Lys
                20                  25                  30

Pro Thr Gln Thr Leu Thr Leu Thr Cys Thr Phe Ser Gly Phe Ser Leu
            35                  40                  45

Ser Thr Ser Gly Met Gly Val Ser Trp Ile Arg Gln Pro Pro Gly Lys
        50                  55                  60

Ala Leu Glu Trp Leu Ala His Ile Tyr Trp Asp Asp Asp Lys Arg Tyr
65                  70                  75                  80

Asn Pro Ser Leu Lys Ser Arg Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Thr Arg Arg Gly Glu Tyr Gly Asn Phe Asp Tyr Trp
        115                 120                 125

Gly Gln Gly Thr Leu Val Thr Val Ser Ser
    130                 135

<210> SEQ ID NO 32
<211> LENGTH: 128
<212> TYPE: PRT
<213> ORGANISM: Artificial Sequence
<220> FEATURE:
<223> OTHER INFORMATION: Synthesized

<400> SEQUENCE: 32

Met Ala Trp Ile Ser Leu Ile Leu Ser Leu Leu Ala Leu Ser Ser Gly
1               5                   10                  15

Ala Ile Ser Gln Thr Val Val Thr Gln Glu Pro Ser Phe Ser Val Ser
                20                  25                  30

Pro Gly Gly Thr Val Thr Leu Thr Cys Arg Ser Ser Gly Ala Val
          35                  40                  45

Thr Thr Ser Asn Phe Ala Asn Trp Val Gln Gln Thr Pro Gly Gln Ala
 50                  55                  60

Pro Arg Gly Leu Ile Gly Gly Thr Asn Asn Arg Ala Pro Gly Val Pro
 65                  70                  75                  80

Asp Arg Phe Ser Gly Ser Leu Leu Gly Asn Lys Ala Ala Leu Thr Ile
              85                  90                  95

Thr Gly Ala Gln Ala Asp Asp Glu Ser Asp Tyr Tyr Cys Ala Leu Trp
          100                 105                 110

Tyr Ser Asn His Trp Val Phe Gly Gly Thr Lys Leu Thr Val Leu
          115                 120                 125

<210> SEQ ID NO 33
<211> LENGTH: 450
<212> TYPE: PRT
<213> ORGANISM: Artificial Sequence
<220> FEATURE:
<223> OTHER INFORMATION: Synthesized

<400> SEQUENCE: 33

Ala Cys Thr Ala Gly Thr Ala Cys Cys Ala Cys Ala Thr Gly Ala
 1               5                  10                  15

Ala Cys Ala Gly Gly Cys Thr Thr Ala Cys Thr Thr Cys Cys Thr Cys
              20                  25                  30

Ala Thr Thr Gly Cys Thr Gly Cys Thr Gly Cys Thr Gly Ala Thr Thr
              35                  40                  45

Gly Thr Cys Cys Cys Thr Gly Cys Ala Thr Ala Thr Gly Thr Cys Cys
 50                  55                  60

Thr Gly Thr Cys Cys Cys Ala Gly Gly Thr Cys Ala Cys Cys Thr Thr
 65                  70                  75                  80

Gly Ala Gly Gly Gly Ala Gly Thr Cys Thr Gly Gly Thr Cys Cys Thr
              85                  90                  95

Gly Cys Cys Cys Thr Gly Gly Thr Gly Ala Ala Ala Cys Cys Cys Ala
              100                 105                 110

Cys Ala Cys Ala Gly Ala Cys Cys Cys Thr Cys Ala Cys Ala Cys Thr
              115                 120                 125

Gly Ala Cys Cys Thr Gly Cys Ala Cys Thr Thr Cys Thr Cys Thr
              130                 135                 140

Gly Gly Gly Thr Thr Cys Thr Cys Ala Cys Thr Cys Ala Gly Cys Ala
 145                 150                 155                 160

Cys Thr Thr Cys Thr Gly Gly Thr Ala Thr Gly Gly Thr Gly Thr
                 165                 170                 175

Gly Ala Gly Cys Thr Gly Gly Ala Thr Cys Ala Gly Ala Cys Ala Gly
              180                 185                 190

Cys Cys Cys Cys Cys Ala Gly Gly Gly Ala Gly Gly Cys Cys Cys
              195                 200                 205

Thr Gly Gly Ala Gly Thr Gly Gly Cys Thr Thr Gly Cys Ala Cys Ala
              210                 215                 220

Cys Ala Thr Thr Thr Ala Cys Thr Gly Gly Gly Ala Thr Gly Ala Thr
 225                 230                 235                 240

Gly Ala Cys Ala Ala Gly Cys Gly Gly Thr Ala Thr Ala Ala Cys Cys
              245                 250                 255

Cys Ala Thr Cys Cys Cys Thr Gly Ala Ala Gly Ala Gly Cys Ala Gly
              260                 265                 270

Gly Cys Thr Cys Ala Cys Cys Ala Thr Cys Thr Cys Ala Ala Gly
            275                 280                 285

Gly Ala Cys Ala Cys Cys Thr Cys Cys Ala Ala Ala Ala Cys Cys
        290                 295                 300

Ala Ala Gly Thr Gly Gly Thr Cys Cys Thr Ala Cys Ala Ala Thr
305                 310                 315                 320

Gly Ala Cys Cys Ala Ala Cys Ala Thr Gly Gly Ala Cys Cys Thr
                325                 330                 335

Gly Thr Cys Gly Ala Cys Ala Cys Ala Gly Cys Cys Ala Cys Cys Thr
            340                 345                 350

Ala Thr Thr Ala Cys Thr Gly Thr Ala Cys Thr Cys Gly Gly Ala Gly
            355                 360                 365

Ala Gly Gly Gly Ala Gly Thr Ala Thr Gly Thr Ala Ala Cys
        370                 375                 380

Thr Thr Cys Gly Ala Cys Thr Ala Cys Thr Gly Gly Gly Cys Cys
385                 390                 395                 400

Ala Gly Gly Gly Ala Ala Cys Cys Cys Thr Gly Gly Thr Cys Ala Cys
                405                 410                 415

Cys Gly Thr Cys Thr Cys Cys Thr Cys Ala Gly Gly Thr Gly Ala Gly
            420                 425                 430

Thr Cys Thr Gly Cys Thr Gly Thr Ala Cys Thr Gly Ala Ala Gly Cys
        435                 440                 445

Thr Thr
    450

<210> SEQ ID NO 34
<211> LENGTH: 420
<212> TYPE: PRT
<213> ORGANISM: Artificial Sequence
<220> FEATURE:
<223> OTHER INFORMATION: Synthesized

<400> SEQUENCE: 34

Gly Cys Thr Ala Gly Cys Ala Cys Cys Ala Cys Cys Ala Thr Gly Gly
1               5                   10                  15

Cys Cys Thr Gly Gly Ala Thr Thr Thr Cys Ala Cys Thr Thr Ala Thr
            20                  25                  30

Cys Cys Thr Cys Thr Cys Thr Cys Cys Thr Gly Gly Cys Thr
        35                  40                  45

Cys Thr Cys Ala Gly Cys Thr Cys Ala Gly Gly Gly Cys Cys Ala
    50                  55                  60

Thr Thr Thr Cys Cys Cys Ala Gly Ala Cys Thr Gly Thr Cys Gly Thr
65                  70                  75                  80

Gly Ala Cys Cys Cys Ala Gly Gly Ala Gly Cys Cys Ala Thr Cys Cys
                85                  90                  95

Thr Thr Cys Thr Cys Ala Gly Thr Gly Thr Cys Cys Cys Cys Thr Gly
            100                 105                 110

Gly Ala Gly Gly Gly Ala Cys Ala Gly Thr Cys Ala Cys Ala Cys Thr
        115                 120                 125

Cys Ala Cys Thr Thr Gly Thr Cys Gly Cys Thr Cys Ala Ala Gly Thr
    130                 135                 140

Thr Cys Thr Gly Gly Gly Gly Cys Thr Gly Thr Thr Ala Cys Ala Ala
145                 150                 155                 160

Cys Cys Ala Gly Thr Ala Cys Thr Thr Thr Gly Cys Cys Ala Ala
                165                 170                 175

```
Cys Thr Gly Gly Gly Thr Cys Cys Ala Gly Cys Ala Gly Ala Cys Cys
            180                 185                 190

Cys Cys Ala Gly Gly Cys Cys Ala Gly Gly Cys Thr Cys Cys Ala Cys
        195                 200                 205

Gly Cys Gly Gly Cys Cys Thr Cys Ala Thr Cys Gly Gly Cys Gly Gly
    210                 215                 220

Thr Ala Cys Cys Ala Ala Cys Ala Ala Cys Cys Gly Ala Gly Cys Thr
225                 230                 235                 240

Cys Cys Ala Gly Gly Gly Gly Thr Cys Cys Cys Thr Gly Ala Thr Cys
                245                 250                 255

Gly Cys Thr Thr Cys Thr Cys Thr Gly Gly Cys Thr Cys Cys Ala Thr
            260                 265                 270

Cys Cys Thr Thr Gly Gly Gly Ala Ala Cys Ala Ala Ala Gly Cys Thr
        275                 280                 285

Gly Cys Cys Cys Thr Cys Ala Cys Cys Ala Thr Cys Ala Cys Cys Gly
    290                 295                 300

Gly Gly Gly Cys Cys Cys Ala Gly Gly Cys Ala Gly Ala Thr Gly Ala
305                 310                 315                 320

Thr Gly Ala Ala Thr Cys Thr Gly Ala Thr Thr Ala Thr Thr Ala Cys
                325                 330                 335

Thr Gly Thr Gly Cys Thr Cys Thr Ala Thr Gly Gly Thr Ala Cys Ala
            340                 345                 350

Gly Cys Ala Ala Cys Cys Ala Cys Thr Gly Gly Gly Thr Gly Thr Thr
        355                 360                 365

Cys Gly Gly Cys Gly Gly Ala Gly Gly Gly Ala Cys Cys Ala Ala Gly
    370                 375                 380

Cys Thr Gly Ala Cys Cys Gly Thr Cys Cys Thr Ala Gly Gly Thr Gly
385                 390                 395                 400

Ala Gly Thr Cys Thr Cys Thr Thr Cys Thr Cys Cys Cys Cys Gly Ala
                405                 410                 415

Ala Thr Thr Cys
            420

<210> SEQ ID NO 35
<211> LENGTH: 449
<212> TYPE: PRT
<213> ORGANISM: Artificial Sequence
<220> FEATURE:
<223> OTHER INFORMATION: Synthesized

<400> SEQUENCE: 35

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Thr Arg Arg Gly Glu Tyr Gly Asn Phe Asp Tyr Trp Gly Gln Gly
            100                 105                 110
```

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 36
<211> LENGTH: 215
<212> TYPE: PRT
<213> ORGANISM: Artificial Sequence
<220> FEATURE:
<223> OTHER INFORMATION: Synthesized

<400> SEQUENCE: 36

Gln Thr Val Val Thr Gln Glu Pro Ser Phe Ser Val Ser Pro Gly Gly
 1               5                  10                  15

```
Thr Val Thr Leu Thr Cys Arg Ser Ser Ser Gly Ala Val Thr Thr Ser
             20                  25                  30

Asn Phe Ala Asn Trp Val Gln Gln Thr Pro Gly Gln Ala Pro Arg Gly
         35                  40                  45

Leu Ile Gly Gly Thr Asn Asn Arg Ala Pro Gly Val Pro Asp Arg Phe
     50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Ala Leu Trp Tyr Ser Asn
                 85                  90                  95

His Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 37
<211> LENGTH: 497
<212> TYPE: PRT
<213> ORGANISM: Artificial Sequence
<220> FEATURE:
<223> OTHER INFORMATION: Synthesized

<400> SEQUENCE: 37

Gln Thr Val Val Thr Gln Glu Pro Ser Phe Ser Val Ser Pro Gly Gly
 1               5                  10                  15

Thr Val Thr Leu Thr Cys Arg Ser Ser Ser Gly Ala Val Thr Thr Ser
             20                  25                  30

Asn Phe Ala Asn Trp Val Gln Gln Thr Pro Gly Gln Ala Pro Arg Gly
         35                  40                  45

Leu Ile Gly Gly Thr Asn Asn Arg Ala Pro Gly Val Pro Asp Arg Phe
     50                  55                  60

Ser Gly Ser Leu Leu Gly Asn Lys Ala Ala Leu Thr Ile Thr Gly Ala
 65                  70                  75                  80

Gln Ala Asp Asp Glu Ser Asp Tyr Tyr Cys Ala Leu Trp Tyr Ser Asn
                 85                  90                  95

His Trp Val Phe Gly Gly Gly Thr Lys Leu Thr Val Leu Gly Gly Gly
            100                 105                 110

Gly Ser Gly Gly Gly Gly Ser Gly Gly Gly Ser Gln Val Thr Leu
        115                 120                 125

Arg Glu Ser Gly Pro Ala Leu Val Lys Pro Thr Gln Thr Leu Thr Leu
    130                 135                 140

Thr Cys Thr Phe Ser Gly Phe Ser Leu Ser Thr Ser Gly Met Gly Val
145                 150                 155                 160
```

-continued

```
Ser Trp Ile Arg Gln Pro Pro Gly Lys Ala Leu Glu Trp Leu Ala His
                165                 170                 175
Ile Tyr Trp Asp Asp Lys Arg Tyr Asn Pro Ser Leu Lys Ser Arg
            180                 185                 190
Leu Thr Ile Ser Lys Asp Thr Ser Lys Asn Gln Val Val Leu Thr Met
        195                 200                 205
Thr Asn Met Asp Pro Val Asp Thr Ala Thr Tyr Tyr Cys Thr Arg Arg
    210                 215                 220
Gly Glu Tyr Gly Asn Phe Asp Tyr Trp Gly Gln Gly Thr Leu Val Thr
225                 230                 235                 240
Val Ser Ser Thr Gly Gly Glu Pro Lys Ser Cys Asp Lys Thr His
            245                 250                 255
Thr Cys Pro Pro Cys Pro Ala Pro Glu Leu Leu Gly Gly Pro Ser Val
        260                 265                 270
Phe Leu Phe Pro Pro Lys Pro Lys Asp Thr Leu Met Ile Ser Arg Thr
    275                 280                 285
Pro Glu Val Thr Cys Val Val Val Asp Val Ser His Glu Asp Pro Glu
290                 295                 300
Val Lys Phe Asn Trp Tyr Cys Asp Gly Val Glu Val His Asn Ala Lys
305                 310                 315                 320
Thr Lys Pro Arg Glu Glu Gln Tyr Asn Ser Thr Tyr Arg Val Val Ser
            325                 330                 335
Val Leu Thr Val Leu His Gln Asp Trp Leu Asn Gly Lys Glu Tyr Lys
        340                 345                 350
Cys Lys Val Ser Asn Lys Ala Leu Pro Ala Pro Ile Glu Lys Thr Ile
    355                 360                 365
Ser Lys Ala Lys Gly Gln Pro Arg Glu Pro Gln Val Tyr Thr Leu Pro
370                 375                 380
Pro Ser Arg Asp Glu Leu Thr Lys Asn Gln Val Ser Leu Thr Cys Leu
385                 390                 395                 400
Val Lys Gly Phe Tyr Pro Ser Asp Ile Ala Val Glu Trp Glu Ser Asn
            405                 410                 415
Gly Gln Pro Glu Asn Asn Tyr Lys Thr Thr Pro Pro Val Leu Asp Ser
        420                 425                 430
Asp Gly Ser Phe Phe Leu Tyr Ser Lys Leu Thr Val Asp Lys Ser Arg
    435                 440                 445
Trp Gln Gln Gly Asn Val Phe Ser Cys Ser Val Met His Glu Ala Leu
450                 455                 460
His Asn His Tyr Thr Gln Lys Ser Leu Ser Leu Ser Pro Gly Lys Pro
465                 470                 475                 480
Thr Leu Tyr Asn Val Ser Leu Val Met Ser Asp Thr Ala Gly Thr Cys
            485                 490                 495
Tyr

<210> SEQ ID NO 38
<211> LENGTH: 127
<212> TYPE: PRT
<213> ORGANISM: Artificial Sequence
<220> FEATURE:
<223> OTHER INFORMATION: Synthesized

<400> SEQUENCE: 38

Met Glu Ser Gln Ile Gln Ala Phe Val Phe Val Phe Leu Trp Leu Ser
1               5                   10                  15
Gly Val Asp Gly Asp Ile Gln Met Thr Gln Ser Pro Ser Ser Leu Ser
```

```
                    20                  25                  30
Ala Ser Val Gly Asp Arg Val Thr Ile Thr Cys Lys Ala Ser Gln Asp
                35                  40                  45

Val Asn Thr Ala Ala Ala Trp Tyr Gln Gln Lys Pro Gly Lys Ala Pro
        50                  55                  60

Lys Leu Leu Ile Tyr Trp Ala Ser Thr Arg His Thr Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln His Tyr
                100                 105                 110

Ser Thr Pro Tyr Thr Phe Gly Gln Gly Thr Lys Leu Glu Ile Lys
                115                 120                 125

<210> SEQ ID NO 39
<211> LENGTH: 11
<212> TYPE: PRT
<213> ORGANISM: Artificial Sequence
<220> FEATURE:
<223> OTHER INFORMATION: Synthesized

<400> SEQUENCE: 39

Lys Ala Ser Gln Asp Val Asn Thr Ala Ala Ala
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Synthesized

<400> SEQUENCE: 40

Trp Ala Ser Thr Arg His Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Synthesized

<400> SEQUENCE: 41

Gln Gln His Tyr Ser Thr Pro Tyr Thr
1               5

<210> SEQ ID NO 42
<211> LENGTH: 139
<212> TYPE: PRT
<213> ORGANISM: Artificial Sequence
<220> FEATURE:
<223> OTHER INFORMATION: Synthesized

<400> SEQUENCE: 42

Met Glu Trp Cys Trp Val Phe Leu Phe Leu Leu Ser Val Thr Ala Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Ile Ile His Trp Val Arg Gln Ala Pro Gly Gln Gly Leu
```

```
                    50                  55                  60
Glu Trp Ile Gly Trp Phe Tyr Pro Gly Asn Asn Asn Ile Lys Ser Asn
 65                  70                  75                  80

Glu Lys Phe Lys Asp Arg Val Thr Leu Thr Ala Asp Thr Ser Thr Ser
                 85                  90                  95

Thr Val Tyr Met Glu Leu Ser Ser Leu Arg Ser Glu Asp Thr Ala Val
            100                 105                 110

Tyr Tyr Cys Ala Arg Asn Glu Asp Asn Tyr Gly Asn Phe Phe Gly Tyr
        115                 120                 125

Trp Gly Gln Gly Thr Leu Val Thr Val Ser Ser
    130                 135

<210> SEQ ID NO 43
<211> LENGTH: 5
<212> TYPE: PRT
<213> ORGANISM: Artificial Sequence
<220> FEATURE:
<223> OTHER INFORMATION: Synthesized

<400> SEQUENCE: 43

Asp Tyr Ile Ile His
 1               5

<210> SEQ ID NO 44
<211> LENGTH: 17
<212> TYPE: PRT
<213> ORGANISM: Artificial Sequence
<220> FEATURE:
<223> OTHER INFORMATION: Synthesized

<400> SEQUENCE: 44

Trp Phe Tyr Pro Gly Asn Asn Asn Ile Lys Ser Asn Glu Lys Phe Lys
 1               5                  10                  15

Asp

<210> SEQ ID NO 45
<211> LENGTH: 11
<212> TYPE: PRT
<213> ORGANISM: Artificial Sequence
<220> FEATURE:
<223> OTHER INFORMATION: Synthesized

<400> SEQUENCE: 45

Asn Glu Asp Asn Tyr Gly Asn Phe Phe Gly Tyr
 1               5                  10

<210> SEQ ID NO 46
<211> LENGTH: 496
<212> TYPE: PRT
<213> ORGANISM: Artificial Sequence
<220> FEATURE:
<223> OTHER INFORMATION: Synthesized

<400> SEQUENCE: 46

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Asn Thr Ala
             20                  25                  30

Ala Ala Trp Tyr Gln Gln Lys Pro Gly Lys Ala Pro Lys Leu Leu Ile
         35                  40                  45

Tyr Trp Ala Ser Thr Arg His Thr Gly Val Pro Ser Arg Phe Ser Gly
     50                  55                  60
```

-continued

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Val Gln
            115                 120                 125

Ser Gly Ala Glu Val Lys Lys Pro Gly Ala Ser Val Lys Val Ser Cys
130                 135                 140

Lys Ala Ser Gly Tyr Thr Phe Thr Asp Tyr Ile Ile His Trp Val Arg
145                 150                 155                 160

Gln Ala Pro Gly Gln Gly Leu Glu Trp Ile Gly Trp Phe Tyr Pro Gly
                165                 170                 175

Asn Asn Asn Ile Lys Ser Asn Glu Lys Phe Lys Asp Arg Val Thr Leu
            180                 185                 190

Thr Ala Asp Thr Ser Thr Ser Thr Val Tyr Met Glu Leu Ser Ser Leu
        195                 200                 205

Arg Ser Glu Asp Thr Ala Val Tyr Tyr Cys Ala Arg Asn Glu Asp Asn
210                 215                 220

Tyr Gly Asn Phe Phe Gly Tyr Trp Gly Gln Gly Thr Leu Val Thr Val
225                 230                 235                 240

Ser Ser Thr Gly Gly Gly Glu Pro Lys Ser Cys Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
290                 295                 300

Lys Phe Asn Trp Tyr Cys Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Gly Lys Pro Thr
465                 470                 475                 480

```
Leu Tyr Asn Val Ser Leu Val Met Ser Asp Thr Ala Gly Thr Cys Tyr
            485                 490                 495
```

<210> SEQ ID NO 47
<211> LENGTH: 267
<212> TYPE: PRT
<213> ORGANISM: Artificial Sequence
<220> FEATURE:
<223> OTHER INFORMATION: Synthesized

<400> SEQUENCE: 47

```
Ala Leu Ile Thr Gln Gln Asp Leu Ala Pro Gln Gln Arg Ala Ala Pro
  1               5                  10                  15

Gln Gln Lys Arg Ser Ser Pro Ser Glu Gly Leu Cys Pro Pro Gly His
             20                  25                  30

His Ile Ser Glu Asp Gly Arg Asp Cys Ile Ser Cys Lys Tyr Gly Gln
         35                  40                  45

Asp Tyr Ser Thr His Trp Asn Asp Leu Leu Phe Cys Leu Arg Cys Thr
     50                  55                  60

Arg Cys Asp Ser Gly Glu Val Glu Leu Ser Pro Cys Thr Thr Thr Arg
 65                  70                  75                  80

Asn Thr Val Cys Gln Cys Glu Glu Gly Thr Phe Arg Glu Glu Asp Ser
                 85                  90                  95

Pro Glu Met Cys Arg Lys Cys Arg Thr Gly Cys Pro Arg Gly Met Val
            100                 105                 110

Lys Val Gly Asp Cys Thr Pro Trp Ser Asp Ile Glu Cys Val His Lys
        115                 120                 125

Glu Ser Gly Thr Lys His Ser Gly Glu Ala Pro Ala Val Glu Glu Thr
130                 135                 140

Val Thr Ser Ser Pro Gly Thr Pro Ala Ser Pro Cys Ser Thr Gly Gly
145                 150                 155                 160

Gly Gly Gln Pro Lys Ala Ala Pro Ser Val Thr Leu Phe Pro Pro Ser
                165                 170                 175

Ser Glu Glu Leu Gln Ala Asn Lys Ala Thr Leu Val Cys Leu Ile Ser
            180                 185                 190

Asp Phe Tyr Pro Gly Ala Val Thr Val Ala Trp Lys Ala Asp Ser Ser
        195                 200                 205

Pro Val Lys Ala Gly Val Glu Thr Thr Thr Pro Ser Lys Gln Ser Asn
    210                 215                 220

Asn Lys Tyr Ala Ala Ser Ser Tyr Leu Ser Leu Thr Pro Glu Gln Trp
225                 230                 235                 240

Lys Ser His Arg Ser Tyr Ser Cys Gln Val Thr His Glu Gly Ser Thr
                245                 250                 255

Val Glu Lys Thr Val Ala Pro Thr Glu Ser Ser
            260                 265
```

<210> SEQ ID NO 48
<211> LENGTH: 98
<212> TYPE: PRT
<213> ORGANISM: Artificial Sequence
<220> FEATURE:
<223> OTHER INFORMATION: Synthesized

<400> SEQUENCE: 48

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 49
<211> LENGTH: 15
<212> TYPE: PRT
<213> ORGANISM: Artificial Sequence
<220> FEATURE:
<223> OTHER INFORMATION: Synthesized

<400> SEQUENCE: 49

Glu Pro Lys Ser Cys Asp Lys Thr His Thr Cys Pro Pro Cys Pro
 1               5                  10                  15

<210> SEQ ID NO 50
<211> LENGTH: 110
<212> TYPE: PRT
<213> ORGANISM: Artificial Sequence
<220> FEATURE:
<223> OTHER INFORMATION: Synthesized

<400> SEQUENCE: 50

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 51
<211> LENGTH: 107
<212> TYPE: PRT
<213> ORGANISM: Artificial Sequence
<220> FEATURE:
<223> OTHER INFORMATION: Synthesized

<400> SEQUENCE: 51

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
             20                  25                  30

Tyr Pro Ser Asp Ile Ala Val Glu Trp Glu Ser Asn Gly Gln Pro Glu
         35                  40                  45

Asn Asn Tyr Lys Thr Thr Pro Pro Val Leu Asp Ser Asp Gly Ser Phe
```

```
                    50                  55                  60
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 52
<211> LENGTH: 98
<212> TYPE: PRT
<213> ORGANISM: Artificial Sequence
<220> FEATURE:
<223> OTHER INFORMATION: Synthesized

<400> SEQUENCE: 52

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val

<210> SEQ ID NO 53
<211> LENGTH: 12
<212> TYPE: PRT
<213> ORGANISM: Artificial Sequence
<220> FEATURE:
<223> OTHER INFORMATION: Synthesized

<400> SEQUENCE: 53

Glu Arg Lys Cys Cys Val Glu Cys Pro Pro Cys Pro
  1               5                  10

<210> SEQ ID NO 54
<211> LENGTH: 109
<212> TYPE: PRT
<213> ORGANISM: Artificial Sequence
<220> FEATURE:
<223> OTHER INFORMATION: Synthesized

<400> SEQUENCE: 54

Ala Pro Pro Val Ala Gly Pro Ser Val Phe Leu Phe Pro Pro Lys Pro
  1               5                  10                  15

Lys Asp Thr Leu Met Ile Ser Arg Thr Pro Glu Val Thr Cys Val Val
                 20                  25                  30

Val Asp Val Ser His Glu Asp Pro Glu Val Gln Phe Asn Trp Tyr Val
             35                  40                  45

Asp Gly Val Glu Val His Asn Ala Lys Thr Lys Pro Arg Glu Glu Gln
 50                  55                  60

Phe Asn Ser Thr Phe Arg Val Val Ser Val Leu Thr Val Val His Gln
 65                  70                  75                  80
```

Asp Trp Leu Asn Gly Lys Glu Tyr Lys Cys Lys Val Ser Asn Lys Gly
            85                  90                  95

Leu Pro Ala Pro Ile Glu Lys Thr Ile Ser Lys Thr Lys
            100                 105

<210> SEQ ID NO 55
<211> LENGTH: 107
<212> TYPE: PRT
<213> ORGANISM: Artificial Sequence
<220> FEATURE:
<223> OTHER INFORMATION: Synthesized

<400> SEQUENCE: 55

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 56
<211> LENGTH: 98
<212> TYPE: PRT
<213> ORGANISM: Artificial Sequence
<220> FEATURE:
<223> OTHER INFORMATION: Synthesized

<400> SEQUENCE: 56

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 57
<211> LENGTH: 62
<212> TYPE: PRT
<213> ORGANISM: Artificial Sequence
<220> FEATURE:
<223> OTHER INFORMATION: Synthesized

<400> SEQUENCE: 57

Glu Leu Lys Thr Pro Leu Gly Asp Thr Thr His Thr Cys Pro Arg Cys
1               5                   10                  15

-continued

```
Pro Glu Pro Lys Ser Cys Asp Thr Pro Pro Cys Pro Arg Cys Pro
        20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
 50                  55                  60
```

<210> SEQ ID NO 58
<211> LENGTH: 110
<212> TYPE: PRT
<213> ORGANISM: Artificial Sequence
<220> FEATURE:
<223> OTHER INFORMATION: Synthesized

<400> SEQUENCE: 58

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
 50                  55                  60

Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110
```

<210> SEQ ID NO 59
<211> LENGTH: 107
<212> TYPE: PRT
<213> ORGANISM: Artificial Sequence
<220> FEATURE:
<223> OTHER INFORMATION: Synthesized

<400> SEQUENCE: 59

```
Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105
```

<210> SEQ ID NO 60
<211> LENGTH: 98
<212> TYPE: PRT
<213> ORGANISM: Artificial Sequence
<220> FEATURE:
<223> OTHER INFORMATION: Synthesized

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 61
<211> LENGTH: 12
<212> TYPE: PRT
<213> ORGANISM: Artificial Sequence
<220> FEATURE:
<223> OTHER INFORMATION: Synthesized

<400> SEQUENCE: 61

Glu Ser Lys Tyr Gly Pro Pro Cys Pro Ser Cys Pro
1               5                   10

<210> SEQ ID NO 62
<211> LENGTH: 110
<212> TYPE: PRT
<213> ORGANISM: Artificial Sequence
<220> FEATURE:
<223> OTHER INFORMATION: Synthesized

<400> SEQUENCE: 62

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 63
<211> LENGTH: 107
<212> TYPE: PRT
<213> ORGANISM: Artificial Sequence
<220> FEATURE:
<223> OTHER INFORMATION: Synthesized

<400> SEQUENCE: 63

Gly Gln Pro Arg Glu Pro Gln Val Tyr Thr Leu Pro Pro Ser Gln Glu
1               5                   10                  15

```
Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Leu Gly Lys
            100                 105

<210> SEQ ID NO 64
<211> LENGTH: 18
<212> TYPE: PRT
<213> ORGANISM: Homo sapiens

<400> SEQUENCE: 64

Pro Thr Leu Tyr Asn Val Ser Leu Val Met Ser Asp Thr Ala Gly Thr
 1               5                  10                  15

Cys Tyr

<210> SEQ ID NO 65
<211> LENGTH: 159
<212> TYPE: PRT
<213> ORGANISM: Artificial Sequence
<220> FEATURE:
<223> OTHER INFORMATION: Synthesized

<400> SEQUENCE: 65

Met Lys Asn His Leu Leu Phe Trp Gly Val Leu Ala Val Phe Ile Lys
 1               5                  10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Arg Ile Ile Val
 50                  55                  60

Pro Leu Asn Asn Arg Glu Asn Ile Ser Asp Pro Thr Ser Pro Leu Arg
 65                  70                  75                  80

Thr Arg Phe Val Tyr His Leu Ser Asp Leu Cys Lys Lys Cys Asp Pro
                 85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
            115                 120                 125

Asn Lys Cys Tyr Thr Ala Val Val Pro Leu Val Tyr Gly Gly Glu Thr
            130                 135                 140

Lys Met Val Glu Thr Ala Leu Thr Pro Asp Ala Cys Tyr Pro Asp
145                 150                 155

<210> SEQ ID NO 66
<211> LENGTH: 4
<212> TYPE: PRT
<213> ORGANISM: Artificial sequence
<220> FEATURE:
<223> OTHER INFORMATION: Synthesized
```

```
<400> SEQUENCE: 66

Gly Gly Ala Ala
1

<210> SEQ ID NO 67
<211> LENGTH: 5
<212> TYPE: PRT
<213> ORGANISM: Artificial sequence
<220> FEATURE:
<223> OTHER INFORMATION: Synthesized

<400> SEQUENCE: 67

Gly Gly Gly Gly Ser
1               5

<210> SEQ ID NO 68
<211> LENGTH: 5
<212> TYPE: PRT
<213> ORGANISM: Artificial sequence
<220> FEATURE:
<223> OTHER INFORMATION: Synthesized

<400> SEQUENCE: 68

Leu Ala Ala Ala Ala
1               5
```